United States Patent [19]

Hutchison et al.

[11] Patent Number: 5,057,506
[45] Date of Patent: Oct. 15, 1991

[54] CERTAIN PHOSPHONIC ACIDS AND DERIVATIVES USEFUL FOR THE TREATMENT OF DISORDERS RESPONSIVE TO N-METHYL-D-ASPARTATE RECEPTOR BLOCKADE

[75] Inventors: Alan J. Hutchison, Verona; Kenneth R. Shaw, Florham Park; Josef A. Schneider, Murray Hill, all of N.J.

[73] Assignee: Ciba-Geigy Corporation, Ardsley, N.Y.

[21] Appl. No.: 441,497

[22] Filed: Nov. 27, 1989

Related U.S. Application Data

[60] Division of Ser. No. 124,226, Nov. 23, 1987, Pat. No. 4,906,621, which is a continuation-in-part of Ser. No. 933,702, Nov. 21, 1986, abandoned, which is a continuation-in-part of Ser. No. 867,114, May 27, 1986, abandoned, which is a continuation-in-part of Ser. No. 738,102, May 24, 1985, abandoned.

[51] Int. Cl.$^5$ .................... C07F 9/572; A61K 31/40
[52] U.S. Cl. ........................ 514/91; 548/413; 546/22; 546/23
[58] Field of Search ............... 548/413; 514/91

[56] References Cited

U.S. PATENT DOCUMENTS

| 4,898,854 | 2/1990 | Hutchison et al. ............ 514/89 |
| 4,906,621 | 3/1990 | Hutchison et al. ............ 514/89 |

FOREIGN PATENT DOCUMENTS

| 203891 | 12/1986 | European Pat. Off. ............ 514/89 |

OTHER PUBLICATIONS

Chem. Abstracts, vol. 104 (9), Abst. No. 104:69130-a Mar. 3, 1986.

Chem. Abstracts, vol. 108(13), Abst. No. 108: 112,734-X, Mar. 28, 1988.
Tetrahedron Letters No. 51, pp. 4929-2930 E. Petrilla Jr. and E. R. Spitz Miller.
Chem. Pharm. Bull. 32 391814 25 (1984).
Phosphorus and Sulfur 1984 vol. 20 pp. 313-321.

*Primary Examiner*—Alan L. Rotman
*Attorney, Agent, or Firm*—Norbert Gruenfeld

[57] ABSTRACT

The present invention is concerned with the phosphonic acids of formula I

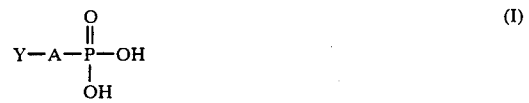

wherein one or both of the acidic hydroxy groups of the phosphonic acid moiety may be functionalized in form of pharmaceutically acceptable mono- or di- esters; wherein Y represent optionally substituted 2-carboxypyrrolidinyl, 2-carboxy-2,5-dihydropyrrolyl, 2-carboxy-1,2,3,6-tetrahydropyridinyl, 2-carboxy-1,2,5,6-tetrahydropyridinyl, 2-carboxypiperidinyl, 2-carboxyetrahydroquinolinyl or 2-carboxyperhydroquinolinyl, 2-carboxyl-2,3-dihydroindolyl or 2-carboxyperhydroindolyl as described herein, and in each of which the carboxy group may be functionalized in form of a pharmaceutical acceptable ester or amide; A represents a direct bond, lower alkenylene, lower alkylidene or lower alkylene provided that A does not represent a direct bond when Y represents 2-carboxypyrolidinyl; and pharmaceutically acceptable salts thereof; which are useful for the treatment of nervous system disorders in mammals and as antagonists of the N-methyl-D-aspartate sensitive excitatory amino acid receptor.

11 Claims, No Drawings

CERTAIN PHOSPHONIC ACIDS AND DERIVATIVES USEFUL FOR THE TREATMENT OF DISORDERS RESPONSIVE TO N-METHYL-D-ASPARTATE RECEPTOR BLOCKADE

CROSS-REFERENCE TO RELATED APPLICATIONS

This is a Divisional of application Ser. No. 124,226 now U.S. Pat. No. 4,906,621 filed on Nov. 23, 1987 which is a continuation-in-part of Ser. No. 933,702 filed Nov. 21, 1986, abandoned, which is a continuation-in-part of application Ser. No. 867,114 filed May 27, 1986, abandoned, which is a continuation-in-part of application Ser. No. 738,102 filed May 24, 1985, abandoned.

SUMMARY OF THE INVENTION

The present invention is concerned with the phosphonic acids of formula I

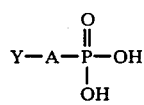

wherein one or both of the acidic hydroxy groups of the phosphonic acid moiety may be functionalized in form of pharmaceutically acceptable mono- or di- esters; wherein Y represents optionally substituted 2-carboxypyrrolidinyl, 2-carboxy-2,5-dihydropyrrolyl, 2-carboxy-1,2,3,6-tetrahydropyridinyl, 2-carboxy-1,2,5,6-tetrahydropyridinyl, 2-carboxypiperidinyl, 2-carboxytetrahydroquinolinyl, 2-carboxyperhydroquinolinyl, 2-carboxy-2,3-dihydroindolyl or 2-carboxy-perhydroindolyl as described herein, and in each of which the carboxy group may be functionalized in form of a pharmaceutically acceptable ester or amide; A represents a direct bond, lower alkenylene, lower alkylidene or lower alkylene provided that A does not represent a direct bond when Y represents 2-carboxypyrrolidinyl; and pharmaceutically acceptable salts thereof; which are useful in mammals as antagonists of the N-methyl-D-aspartate sensitive excitatory amino acid receptor.

The instant invention is further concerned with process for preparing said compounds, with pharmaceutical compositions comprising said compounds, with a method of blocking the N-methyl-D-aspartate excitatory amino acid receptor, and with a method of treating conditions and diseases in mammals responsive to the effect of an excitatory amino acid receptor antagonist by administration of said compounds or of pharmaceutical compositions comprising said compounds.

The compounds of the invention are active and useful as selective antagonists of the N-methyl-D-aspartate (NMDA) excitatory amino acid receptor. The compounds of the invention are therefore also useful, administered alone or in combination to mammals, for the treatment of disorders responsive to said blockade of the NMDA receptor, comprising e.g. cerebral ischemia, muscular spasms (spasticity), convulsive disorders (epilepsy) and anxiety. The compounds of the invention are also contemplated to be useful for the treatment of Huntington's disease.

DETAILED DESCRIPTION OF THE INVENTION

One aspect of the invention relates to the phosphonic acid derivatives of formula I and derivatives thereof wherein Y represents optionally substituted 2-carboxypiperidinyl, 2-carboxy-1,2,3,6-tetrahydropyridinyl or 2-carboxy-1,2,5,6-tetrahydropyridinyl, more specifically the compounds of the formula II

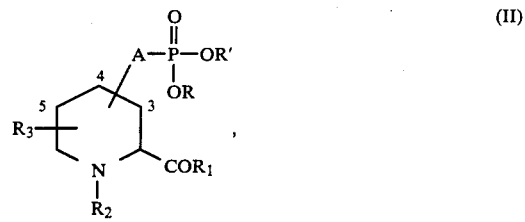

and the compounds of formula II with a double bond present between the 3 and 4 or between the 4 and 5 carbon atoms of the piperidyl ring, in which the phosphono bearing chain is attached at the 3, 4, or 5- position of the piperidinyl or tetrahydropyridinyl ring, and wherein R and R' represent hydrogen, lower alkyl, benzyl, benzyl substituted on phenyl by halogen, lower alkyl or lower alkoxy, lower alkanoyloxymethyl, lower alkanoyloxymethyl substituted on oxymethyl by lower alkyl, cyclohexyl or cyclopentyl; $R_2$ represents hydrogen, lower alkyl, aryl-lower alkyl, or acyl; $R_3$ represents hydrogen, lower alkyl or aryl-lower alkyl; $COR_1$ represents carboxy or carboxy derivatized in the form of a pharmaceutically acceptable ester or amide; A represents a direct bond, lower alkenylene, or lower alkylene; and pharmaceutically acceptable salts thereof.

Preferred are the said compounds, and more particularly those of formula II, wherein R and R' independently represent hydrogen, benzyl, lower alkyl, lower alkanoyloxymethyl or lower alkanoyloxymethyl substituted on oxymethyl by lower alkyl, cyclohexyl or cyclopentyl; A represents a direct bond or alkylene of 1 to 4 carbon atoms; $COR_1$ represents carboxy, carbamoyl or carboxy esterified in form of a pharmaceutically acceptable ester; $R_2$ and $R_3$ represent hydrogen or lower alkyl; and pharmaceutically acceptable salts thereof.

Also preferred are compounds of formula II wherein A represents alkenylene of 2 to 4 carbon atoms; and R, R', $COR_1$, $R_2$ and $R_3$ have meaning as defined above.

Further preferred are the compounds of formula II wherein R and R' represent hydrogen, lower alkanoyloxymethyl or lower alkanoyloxymethyl substituted on oxymethyl by lower alkyl; A is at the 4- position and represents a direct bond or alkylene of 1 to 4 carbon atoms; $R_2$ and $R_3$ represent hydrogen; $COR_1$ represents carboxy, carbamoyl or carboxy esterified in form of a pharmaceutically acceptable ester; and pharmaceutically acceptable salts thereof.

Also further preferred are compounds of formula II wherein A represents alkenylene of 3 or 4 carbon atoms with double bond adjacent to phosphono grouping, and R, R', $COR_1$, $R_2$ and $R_3$ have meaning as defined above.

Particularly preferred are the compounds of formula III

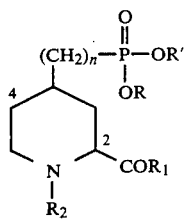

wherein n represents the integer 1, 2, or 3; R and R' independently represent hydrogen, lower alkyl, benzyl, lower alkanoyloxymethyl or lower alkanoyloxymethyl substituted on oxymethyl by lower alkyl; $COR_1$ represents carboxy, carboxy esterified in the form of a pharmaceutically acceptable ester, or carbamoyl; $R_2$ represents hydrogen, lower alkyl, lower alkanoyl, benzoyl or benzoyl substituted by lower alkyl, by lower alkoxy, by halogen or by trifluoromethyl; and pharmaceutically acceptable salts of said compounds having a salt-forming functional grouping.

Most preferred are the compounds of formula III wherein the 2- and 4- substituents are cis to each other.

Further preferred are the said compounds of formula III wherein n represents the integer 1, 2 or 3; R and R' both represent hydrogen or lower alkanoyloxymethyl; or one of R and R' represents hydrogen and the other of R and R' represents lower alkyl, benzyl, lower alkanoyloxymethyl or lower alkanoyloxymethyl substituted on oxymethyl by lower alkyl; $R_2$ represents hydrogen; $COR_1$ represents carboxy or carboxy esterified in form of a pharmaceutically acceptable ester; and pharmaceutically acceptable salts thereof.

A preferred embodiment relates to the compounds, preferably cis, of formula III wherein n represents the integer 1, 2 or 3; R and R' represent hydrogen; $COR_1$ represents carboxy or carboxy esterified in form of a pharmaceutically acceptable ester; $R_2$ represents hydrogen; and pharmaceutically acceptable salts thereof.

A further preferred embodiment relates to the

Compounds of formula II, preferably cis, in which R, R', $R_2$ and $R_3$ represent hydrogen; A is at the 4-position and represents 1,3-propenylene, preferably with double bond adjacent to the phosphono grouping; $COR_1$ represents carboxy or carboxy esterified in form of a pharmaceutically acceptable ester; and pharmaceutically acceptable salts thereof. A further particular embodiment relates to said compounds of formula II wherein A represents 1,3-propenylene with double bond adjacent to the piperidine ring.

Another aspect of the invention relates to the phosphonic acid derivatives of formula I and derivatives cited above wherein Y represents 2-carboxy-1,2,3,4-tetrahydro- or perhydroquinolinyl in which the phosphono bearing chain is preferably located at the 3 or 4 position of the tetrahydro or perhydroquinolinyl ring, i.e. the compounds of formula IV

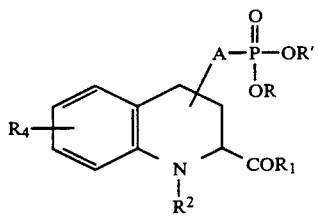

or perhydro derivatives thereof, wherein A represents lower alkylene, lower alkenylene or a direct bond; R and R' represent hydrogen, lower alkyl, benzyl, benzyl substituted on phenyl by halogen, lower alkyl or lower alkoxy; or R and R' represent lower alkanoyloxymethyl, lower alkanoyloxymethyl substituted on oxymethyl by lower alkyl, cyclohexyl or cyclopentyl; $COR_1$ represents carboxy or carboxy functionalized in the form of a pharmaceutically acceptable ester or amide; $R_2$ represents hydrogen, lower alkyl, aryl-lower alkyl, or acyl; $R_4$ represents hydrogen, lower alkyl, lower alkoxy, halogen or trifluoromethyl; and pharmaceutically acceptable salts thereof.

Preferred are the compounds of formula V

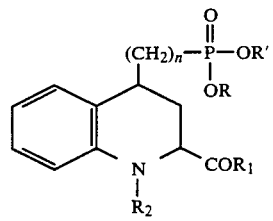

or the perhydroquinoline derivatives thereof wherein n represents the integer 1, 2, or 3; R and R' independently represent hydrogen, lower alkyl, benzyl, lower alkanoyloxymethyl or lower alkanoyloxymethyl substituted on oxymethyl by lower alkyl; $COR_1$ represents carboxy, carboxy esterified in the form of a pharmaceutically acceptable ester, or carbamoyl; $R_2$ represents hydrogen, lower alkyl, lower alkanoyl, benzoyl or benzoyl substituted by lower alkyl, by lower alkoxy, by halogen or by trifluoromethyl; and pharmaceutically acceptable salts of said compounds having a salt-forming functional grouping.

Most preferred are the compounds of formula V wherein the 2- and 4- substituents are cis to each other.

Further preferred are said compounds of formula V and perhydroquinoline derivatives thereof wherein n represents the integer 1, 2 or 3; R and R' both represent hydrogen or lower alkanoyloxymethyl; or one of R and R' represents hydrogen and the other of R and R' represents lower alkyl, benzyl, lower alkanoyloxymethyl, or lower alkanoyloxymethyl substituted on oxymethyl by lower alkyl; $R_2$ represents hydrogen; $COR_1$ represents carboxy or carboxy esterified in form of a pharmaceutically acceptable ester; and pharmaceutically acceptable salts thereof.

A preferred embodiment relates to the compounds, preferably cis, of formula V and the perhydroquinoline derivatives thereof wherein n represents the integer 1; R and R' represent hydrogen; $COR_1$ represents carboxy or carboxy esterified in form of a pharmaceutically acceptable ester; $R_2$ represents hydrogen; and pharmaceutically acceptable salts thereof.

Another preferred embodiment relates to the compounds of formula IV and the perhydroquinoline derivatives thereof wherein A is attached at the 4 position and represents 1,3-propenylene with double bond adjacent to the phosphono grouping; R, R' and $R_2$ and $R_4$ represent hydrogen; $COR_1$ represents carboxy or carboxy esterified in form of a pharmaceutically acceptable ester; and pharmaceutically acceptable salts thereof.

A further aspect of the invention relates to the phosphonic acid derivatives of formula I and derivatives cited above wherein Y represents optionally substituted 2-carboxypyrrolidinyl, i.e. the compounds of formula VI

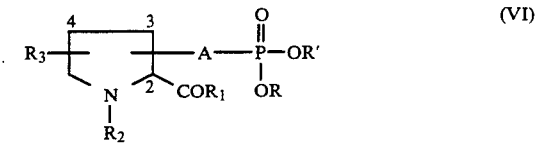

and the compounds of formula VI with a double bond present between the 3 and 4 carbon atoms of the pyrrolidinyl ring, in which the phosphono bearing chain is attached preferably at the 3 or 4 position of the pyrrolidine ring and wherein R and R' represent hydrogen, lower alkyl, benzyl, benzyl substituted on phenyl by halogen, lower alkyl, or lower alkoxy, or R and R' represent lower alkanoyloxymethyl, lower alkanoyloxymethyl substituted on oxymethyl by lower alkyl, cyclohexyl or cyclopentyl; $R_2$ represents hydrogen, lower alkyl, or acyl; $R_3$ represents hydrogen, lower alkyl or aryl-lower alkyl; $COR_1$ represents carboxy or carboxy derivatized in the form of pharmaceutically acceptable ester or amide; A represents lower alkylene or lower alkenylene; and pharmaceutically acceptable salts thereof.

Preferred are the compounds of formula VI wherein the phosphono bearing group is attached at the 3 or 4-position; $R_2$ and $R_3$ represent hydrogen; R and R' represent hydrogen or lower alkanoyloxymethyl; $COR_1$ represents carboxy, carbamoyl or carboxy esterified in form of a pharmaceutically acceptable ester; A represents methylene, ethylene, or propylene; and pharmaceutically acceptable salts.

Further preferred are the compounds of formula VI wherein the phosphono bearing group is attached at the 3-position; $R_2$ and $R_3$ represent hydrogen; R and R' represent hydrogen; $COR_1$ represents carboxy or carboxy esterified in the form of a pharmaceutically acceptable ester; A represents methylene, ethylene or propylene; and pharmaceutically acceptable salts.

Also further preferred are the compounds of formula VI wherein the phosphono bearing group A is attached at the 3-position; R, R', $R_2$, $R_3$ and $COR_1$ have meaning as defined above; and A represents 1,3-propenylene with double bond adjacent to the phosphono grouping; and pharmaceutically acceptable salts thereof.

The general definitions used herein have the following meaning in the context of the invention.

The term "lower", when referred to above and hereinafter in connection with organic groups, radicals or compounds respectively, defines such with up to and including 7, preferably up to and including 4 and advantageously one, two or three carbon atoms.

A lower alkyl group preferably contains 1-4 carbon atoms and represents for example ethyl, propyl, butyl or advantageously methyl.

A lower alkylene linking group preferably contains 1-4 carbon atoms and represents for example methylene, ethylene, propylene, i.e. 1,2- or 1,3-propylene, butylene, i.e. 1,2-, 1,3- or 1,4-butylene.

A lower alkenylene linking group representing A or A' preferably contains 2 to 4 carbon atoms and represents for example ethenylene, 1,3-propenylene, 1,4-but-1-enylene, 1,4-but-2-enylene, advantageously with double bond adjacent to phosphono grouping.

A lower alkylidene linking group representing A or A' preferably contains 1 to 4 carbon atoms and represents for example methylidene, ethylidene, or straight chain propylidene, the double bond being exocyclic to the ring in Y.

A lower alkoxy group preferably contains 1-4 carbon atoms and represents for example, ethoxy, propoxy or advantageously methoxy.

Lower alkanoyl preferably contains 2-7 carbon atoms and represents advantageously acetyl, propionyl, n-butyryl, isobutyryl or pivaloyl.

Lower alkanoyloxy represents advantageously acetoxy, propionyloxy, n- or i- butyryloxy or pivaloyloxy (trimethylacetyloxy).

Halogen is preferably fluorine and chlorine, but may also represent bromine or iodine.

Aroyl represents arylcarbonyl, preferably benzoyl or benzoyl substituted by one to three substituents selected from lower alkyl, lower alkoxy, trifluoromethyl and halogen; or pyridylcarbonyl, particularly nicotinoyl.

Aroyloxy represents preferably benzoyloxy, benzoyloxy substituted on the phenyl ring by lower alkyl, halogen or lower alkoxy, e.g. methyl, chloro or methoxy respectively; or nicotinoyloxy.

Aryl represents preferably optionally substituted phenyl, e.g. phenyl or phenyl substituted by one to three substituents selected from lower alkyl, lower alkoxy, trifluoromethyl and halogen; or pyridyl, particularly 3-pyridyl.

Aryl-lower alkyl represents preferably aryl-$C_1$-$C_4$-alkyl, aryl having meaning as defined above, advantageously benzyl or 2-phenylethyl.

Acyl represents carboxy derived acyl, preferably lower alkanoyl, aryl-lower alkanoyl, aroyl, lower alkoxycarbonyl, aryl-lower alkoxycarbonyl, alpha-amino-lower alkanoyl or alpha-amino-aryl-lower alkanoyl.

Aryl-lower alkanoyl represents preferably aryl-$C_1$-$C_4$-alkanoyl, advantageously phenylacetyl or 3-phenylpropionyl.

A lower alkoxycarbonyl group preferably contains 1-4 carbon atoms in the alkoxy portion and represents for example: methoxycarbonyl, propoxycarbonyl, isopropoxycarbonyl or advantageously ethoxycarbonyl.

An N-mono(lower alkyl)-carbamoyl group preferably contains 1-4 carbon atoms in the alkyl portion and is for example N-methylcarbamoyl, N-propylcarbamoyl, or advantageously N-ethylcarbamoyl.

Aryl-lower alkoxycarbonyl represents preferably benzyloxycarbonyl.

Alpha-amino-lower alkanoyl and alpha-amino-aryl-lower alkanoyl represents acyl groups of alpha-aminoacids, such as alanyl, glycyl, leucyl, isoleucyl, phenylalanyl and the like.

An N,N-di(lower alkyl)-carbamoyl group preferably contains 1-4 carbon atoms in each lower alkyl portion and represents for example N,N-dimethylcarbamoyl, N-methyl-N-ethylcarbamoyl and advantageously N,N-diethylcarbamoyl.

A di-lower alkylamino-N-lower alkylcarbamoyl group preferably represents di-$C_1$-$C_4$-alkylamino-N-$C_2$-$C_4$-alkylcarbamoyl, the two nitrogen atoms being separated by 2-4 carbon atoms and represents for example N-(2-diethylaminoethyl)carbamoyl, N-(3-diethylaminopropyl)carbamoyl.

A mono-lower alkylamino group preferably contains 1-4 carbon atoms and represents for example methylamino, ethylamino, n or i-(propylamino or butylamino).

A di-lower alkylamino group preferably contains 1-4 carbon atoms in each lower alkyl group and represents for example dimethylamino, diethylamino, di-(n-propyl)-amino and di-(n-butyl)-amino).

A di-lower alkylamino - lower alkoxycarbonyl group contains preferably 2–4 carbon atoms in the alkoxy portion, the oxygen and nitrogen atoms being separated by 2–4 carbon atoms, and for example represents N,N-diethylaminoethoxycarbonyl or N,N-diethylaminopropoxycarbonyl.

A pharmaceutically acceptable ester within the context of the present invention represents an ester of a compound of the invention having a carboxy group, preferably a carboxylic acid prodrug ester that may be convertible under physiological conditions to the corresponding free carboxylic acid.

Carboxy esterified in form of a pharmaceutically acceptable ester, preferably represents e.g. lower alkoxycarbonyl; (amino, mono- or di-lower alkylamino)-substituted straight chain $C_2$–$C_5$ lower alkoxycarbonyl; carboxy substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. unsubstituted or substituted benzyloxycarbonyl or pyridylmethoxycarbonyl; lower alkanoyloxy-substituted methoxycarbonyl, e.g. pivaloyloxymethoxycarbonyl; (lower alkanoyloxy or lower alkoxy)-substituted lower alkoxymethoxy carbonyl; bicyclo[2,2,1]heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxylower alkoxycarbonyl, e.g. 1-(methoxy- or ethoxycarbonyloxy)-ethoxycarbonyl.

Most preferred prodrug esters are e.g. the straight chain $C_1$–$C_4$-alkyl esters such as ethyl; the lower alkanoyloxymethyl esters such as pivaloyloxymethyl; the dilower alkylamino-straight chain $C_2$–$C_4$-alkyl esters such as 2-diethyl-aminoethyl; the pyridylmethyl esters such as 3-pyridylmethyl.

A pharmaceutically acceptable amide within the context of the present invention represents an amide of a compound of the invention having a carboxy group, preferably a carboxylic acid amide that may be convertible under physiological conditions to the corresponding free carboxylic acid.

Preferred amides are compounds of the invention wherein carboxy is derivatized as carbamoyl, N-monolower alkylcarbamoyl such as N-ethylcarbamoyl, N,N-di-lower alkylcarbamoyl such as N,N-diethylcarbamoyl, or di-lower aklylamino-N-lower alkylcarbamoyl such as N-(2-diethylaminoethyl)carbamoyl or N-(3-diethylaminopropyl)carbamoyl.

Pharmaceutically acceptable salts are preferably metal or ammonium salts or said compounds of the invention having a free phosphonic or carboxy group, more particularly alkali or alkaline earth metal salts, e.g. the sodium, potassium, magnesium or calcium salt; or advantageously crystallizing ammonium salts derived from ammonia or organic amines, such as methylamine, diethylamine, triethylamine, dicylohexylamine, triethanolamine, ethylenediamine, tris-(hydroxymethyl)aminomethane or benzyltrimethylammonium hydroxide. The compounds of the invention which are basic amines form acid addition salts of preferably pharmaceutically acceptable inorganic or organic acids, such as of strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic or naphthalenesulfonic acid.

The compounds of the invention exhibit valuable pharmacological properties, e.g. by selectively blocking the N-methyl-D-aspartate excitatory aminoacid receptors in mammals. The compounds are thus useful for treating diseases responsive to excitatory amino acid blockade in mammals, comprising e.g. cerebral ischemia and nervous system disorders, particularly convulsive disorders (epilepsy) and anxiety.

These effects are demonstrable in in vitro tests or in vitro animal tests using advantageously mammals or tissues or enzyme preparations thereof, e.g. mice, rats, or monkeys. Said compounds can be administered to them eternally or parentally, advantageously orally or transdermally, or subcutaneously, intravenously or intraperitoneally, for example, within gelatin capsules, or in the form of aqueous suspensions or solutions, respectively. The applied in vivo dosage may range between about 0.01 to 100 mg/kg, preferably between about 0.05 and 50 mg/kg, advantageously between about 0.1 and 10 mg/kg. Said compounds can be applied in vitro in the form of e.g. aqueous solutions and the dosage may range between about $10^{-4}$ molar and $10^{-8}$ molar concentrations.

The inhibitory effect on the NMDA-type excitatory amino acid receptors is determined in vitro by measuring the inhibition of the NMDA-evoked $^3$H-acetylcholine ($^3$H-ACh) release from corpus striatum tissue of rat brain, according to J. Lehmann and B. Scatton, Brain Research 252, 77–89 (1982) and Nature 297, 422–424 (1982).

Antagonists of NMDA-type excitatory amino acid receptors competitively antagonize NMDA-evoked $^3$H-acetylcholine ($^3$H-ACh) release from corpus striatum tissue of the brain.

The inhibition of the NMDA-evoked $^3$H-acetylcholine ($^3$H-ACh) release from rat striatal tissue slices by a compound of the invention is expressed as % of release of $^3$H-ACh in response to stimulation with 50 uM NMDA compared to control. Tests are two-tailed with a minimum of n=4 in each group. In $IC_{50}$ values represent the concentration of test compound required to inhibit the NMDA-increased $^3$H-ACh release by 50%.

Illustrative of the invention, cis-4-phosphonomethyl-2-piperidinecarboxylic acid hydrochloride has an IC50 of about $8 \times 10^{-6}$M in the in vitro NMDA-evoked $^3$H-ACh release test.

The inhibitory effect on the NMDA-type excitatory amino acid receptors is demonstrated in vivo by inhibition of NMDA-induced convulsions in the mouse.

Illustrative of the invention, cis-4-phosphonomethyl-2-piperidinecarboxylic acid hydrochloride prevents NMDA-induced convulsions in the mouse at a dose of about 2.3 mg/kg i.p.; cis 4-[1-(3-phosphonoprop-1-enyl)]-piperidine-2-carboxylic acid is similarly effective at a dose of about 1.2 mg/kg i.p..

Further indicative of the anticonvulsant activity, compounds of the invention are effective in preventing audiogenic-induced seizures in DBA/2 mice (Chapman et al., Arzneim.-Forsch. 34:1261, 1984).

The effect is determined as follows:

Forty-five minutes following compound or vehicle administration, mice are placed individually in a soundproof chamber. After a 30 second accommodation period, the mice are exposed to a sound stimulation of 110 dB for 1 minute or until the appearance of a tonic-clonic seizure. Control seizures consist of an initial wild running phase. The prevention of wild running is indicative of an anticonvulsant effect.

Test compounds in either distilled water solution or in a 3% (w/v) colloidal cornstarch suspension containing 5% (w/v) polyethyleneglycol 400 and 0.34% (w/v) Tween 80, are administered by oral intubation or intraperitoneally in a volume of 10 ml/kg of body weight.

Illustrative of the invention, cis-4-phosphonomethyl-2l-piperidinecarboxylic acid hydrochloride is effective in the audiogenic-induced seizure model in mice with an $ED_{50}$ of about 1.8 mg/kg on i.p. administration.

Indicative of anxiolytic activity, compounds of the invention are effective in the Cook/Davidson conflict model (Psychopharmacologia 15, 159–168 (1969)).

Illustrative of the invention, cis-4-phosphonomethyl-2-piperidine-carboxylic acid is active in the Cook/Davidson test for anxiolytic activity at a dose of about 2 mg/Kg i.p.

The cerebral antiischemic activity, that is the effect of the compounds of the invention in preventing or reducing brain damage in mammals due to a transient cerebral ischemia (as in a stroke) can be determined in the mongolian gerbil ischemia model, e.g. the model described by T. Kirino, Brain Research 239, 57–69 (1982l).

The inhibitory effect on the observed hyperactivity and on the degeneration of neurons in the hippocampus region of the brain following a 5-minute period of ischemia is measured.

The test compound is administered i.p. 15 minutes before the ischemia or 2, 4, and 6 hours post ischemia.

Illustrative of the invention, cis-4-phosphonomethyl-2-piperinecarboxylic acid, at a dose of 10 mg/Kg ip administered either before or after the ischemia episode, inhibits the ischemia-induced hyperactivity of the gerbil and reduces the degeneration of cerebral neurons as measured in the hippocampus region of the brain.

The aforementioned advantageous properties render the compounds of the invention useful as antagonists of the N-methyl-D-aspartate excitatory amino acid receptor in mammals and for the treatment of conditions responsive thereto, such as cerebral ischemia, anxiety and convulsive disorders.

The compounds of the invention, i.e. the compounds of formula I cited hereinabove, are prepared by a) for compounds of formula I wherein A represents a direct bond or lower alkylene, reducing the pyrrolyl, pyridinyl, indolyl or quinolinyl ring in a compound of the formula

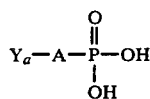   (VII)

or a functional phosphonic acid derivative thereof as defined above, wherein A represents a direct bond or lower alkylene; and wherein $Y_a$ represents an unsaturated form of Y, namely 2-carboxypyrrolyl, 2-carboxypyridinyl, 2-carboxyquinolinyl or 2-carboxyindolyl all optionally substituted as defined for Y, and wherein the carboxy group may be functionalized in form of an ester or amide as defined above; or reducing a double bond in a compound of the formula

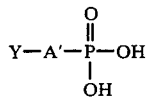   (VIIa)

wherein Y has meaning as defined above, or a functional phosphonic acid derivative thereof, A' represents lower alkenylene or lower alkenylidene with the double bond attached to Y; or b) condensing a reactive ester derivative of a compound of the formula

Y—A—OH   (VIII)

wherein Y and A have meaning as defined above with a diester of phosphorus acid, of the formula IX or with a phosphorus trihalide or a phosphorus tri-(lower)alkoxide of formula X

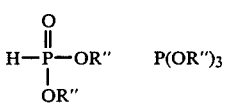

(IX)    (X)

wherein R'' advantageously represents lower alkyl and, if required, converting the resulting phosphonic acid derivative to the phosphonic acid or other ester derivative thereof;

c) converting to $COR_1$ a substituent other than $COR_1$ at position 2 of the piperidinyl, tetrahydro-pyridinyl, 1,2,3,4-tetrahydroquinolinyl, perhydroquinolinyl, dihydropyrrolyl, pyrrolidinyl, 2,3-dihydroindolyl or perhydroindolyl ring in a compound otherwise identical to a compound of the invention; and carrying out the said processes while, if necessary, temporarily protecting any interfering reactive group(s) in these processes, and then liberating the resulting compound of the invention; and, if desired, converting a resulting compound of the invention into another compound of the invention, and/or, if desired, converting a resulting free compound into a salt or a resulting salt into the free compound or into another salt; and/or separating a mixture of isomers or racemates obtained into the single isomers or racemates; and/or, if desired, resolving a racemate obtained into the optical antipodes.

A reactive ester derivative of a compound, in any of the herein mentioned processes, having a hydroxy group, e.g. of a compound of formula VIII, represents a compound wherein hydroxy is esterified by a strong acid, especially hydrochloric, hydrobromic or hydriodic acid, or sulfuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

In starting compounds and intermediates therefore which are converted to the compounds of the invention in a manner described herein, functional groups present, such as carboxy, amino (including ring NH) and hydroxy groups, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

The preparation of the compounds of the invention according to process (a) relating to reduction of a compound of formula VII is carried out by methods known in the art for the reduction of pyrrole, pyridine, indole and quinoline rings. For example, the reduction of the pyridine or quinoline ring is advantageously carried out with an organometallic reducing agent or by catalytic hydrogenation e.g. in the presence of platinum oxide and an acidic solvent such as acetic acid to give corresponding tetrahydropyridines, piperidines, 1,2,3,4-tetrahydroquinolines or perhydroquinolines of the invention, i.e. of formula II, IV and derivatives thereof. Quaternary quinolinium and pyridinium compounds, e.g. in which $R_2$ is lower alkyl or aryl-lower alkyl, may be similarly reduced.

The starting compounds of formula VII, e.g. the quinoline and pyridine derivatives for said process (a) are prepared, e.g., by first condensing a compound $R_3$-substituted-(3,-4- or 5-pyridinyl)-A-OH or $R_4$-substituted-(3-or 4-quinolinyl)-A-OH (A, $R_3$ and $R_4$ having meaning as defined above) in form of a reactive ester derivative, e.g. a halide such as a chloride or bromide, with a diester of formula IX in the presence of a strong base, e.g. as described in Chemical Abstracts 61, 10703, or with a tri-(lower)alkyl phosphite of formula X to give the corresponding

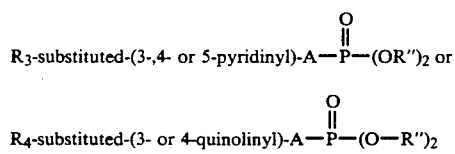

in which A, R", $R_3$ and $R_4$ are as defined hereinabove.

Subsequent treatment with e.g. a peracid, such as m-chloroperbenzoic acid gives the corresponding pyridine-N-oxides or quinoline-N-oxides. Condensation with a reactive cyanide, e.g. a trialkylsilyl cyanide such as trimethylsilyl cyanide, preferably under basic conditions, e.g. in the presence of triethylamine, gives the corresponding 2-cyanopyridine or 2-cyanoquinoline derivatives. The cyano group in the 2-cyanopyridine and 2-cyanoquinoline derivatives are then converted, by methods known in the art, to the 2-$COR_1$ (carboxy, esterified carboxy or optionally substituted carbamoyl substituted)pyridine and quinoline derivatives as defined hereinabove.

Intermediates of formula VII also inhibit the N-methyl-D-aspartate excitatory aminoacid receptors in mammals. Preferred are said compounds of formula VII wherein Ya represents 2-carboxypyridinyl optionally substituted as defined hereinabove.

The preparation of the compounds of formula I and derivatives (wherein A represents lower alkylene) according to process (a) relating to the reduction of the double bond in a compound of formula VIIa, is carried out by e.g. catalytic hydrogenation.

Compounds of formula VIIa are equivalent to the compounds of formula I wherein A represents lower alkenylene or lower alkylidene which, in addition to being useful as intermediates, are also useful as antagonists of the N-methyl-D-aspartate excitatory amino acid receptor as described herein for compounds of the invention.

The compounds of formula VIIa and derivatives thereof may be prepared, e.g. by reacting an aldehyde or ketone (including oxo derivatized Y) with e.g. a tetra-lower alkyl ester of methylenediphosphonic acid under basic conditions, thereby adding the phosphonomethylidene grouping to obtain a compound of formula VIIa (wherein the double bond is adjacent to the phosphono grouping), and by other methods illustrated herein, e.g. using processes b) and c).

The preparation of the compounds of the invention wherein A represents lower alkenylene and wherein the double bond is adjacent to the phosphono grouping involving the condensation of an aldehyde or ketone with e.g. a tetra lower alkyl ester of methylenediphosphonic acid is carried out according to procedure known in the art for such condensations, in the presence of a strong anhydrous base, e.g. butyl lithium, in an inert polar solvent such as tetrahydrofuran, preferably at reflux temperature. The starting aldehydes or ketones can be prepared e.g. by oxidation of the corresponding alcohols for example with pyridinium chlorochromate, or other methods as illustrated in the examples. The aldehydes or ketones so obtained may also be converted to aldehydes or ketones of longer chain length using conventional methodology, e.g. by a Wittig condensation of an aldehyde with methoxy-methyl-triphenyl-phosphonium chloride to yield the homologous aldehyde, and by other well-known sequences of reactions described in the examples.

The condensation according to process (b) is advantageously used for the preparation of the compounds of formula I wherein the double bond within the alkenylene grouping A is not adjacent to the phosphono grouping. The corresponding starting materials of formula VIII and reactive derivatives thereof can be prepared by methods well known in the art, starting from intermediates wherein A represents lower alkylene, the preparation of which is described above. For example, the starting material of formula VIII wherein A represents lower alkenylene is prepared by condensing an aldehyde with a suitable Wittig reagent, e.g. formylmethylene-triphenyl- phosphoran, reducing the resulting unsaturated aldehyde (in which the chain has been lengthened by two carbon atoms) to the alcohol e.g. with sodium borohydride, and converting the resulting unsaturated alcohol to a reactive derivative, e.g. to the bromide with triphenylphosphine/N-bromo-succinimide.

The condensation according to process (b) of a reactive ester derivative of a compound of formula VIII with a compound of formula X, e.g. triethyl phosphite, is carried out, e.g. by heating in an inert solvent, and under conditions known in the art for a Michaelis-Arbuzov reaction according to Angew. Chem. Int. Ed. 16, 477 (1977) and Chem. Rev. 81, 415 (1981). Similarly, condensation with phosphorus trichloride and subsequent hydrolysis gives a compound of formula I.

The condensation according to process (b) of a reactive ester derivative of a compound of formula VIII with a compound of formula IX, e.g. diethylphosphonate (diethyl phosphite), is carried out e.g. in a strong basic medium, for instance in the presence of an alkali metal such as sodium, an alkali metal hydride such as sodium hydride, an alkali metal alkoxide such as potassium t-butoxide, in an inert solvent such as toluene or dimethylformamide.

The starting materials of formula VIII are either known in the art or are prepared by methods known in the art, e.g. by reduction of the corresponding pyridinyl, indolyl and quinolinyl compounds, or as described herein.

Interconversions according to process (c) are carried out by methods well-known in the art.

Groups convertible into a $COR_1$ group are, for example, carboxy groups in form of anhydrides or acid halides, cyano, amidino groups, including cyclic amidino groups such as 5-tetrazolyl, iminoether groups, including cyclic iminoether groups, e.g., dihydro-2-oxazolinyl or dihydro-2-oxazolinyl groups substituted by lower alkyl, and also hydroxymethyl, etherified hydroxymethyl, lower alkanoyloxymethyl, trialkoxymethyl, acetyl, trihaloacetyl, halomethyl, carboxycarbonyl (COCOOH), formyl (CHO), di(lower)alkoxymethyl, alkylenedioxymethyl or vinyl.

Certain terms used in the processes have the meanings as defined below.

Trialkoxymethyl represents preferably tri(lower alkoxy)-methyl, particularly triethoxy- or trimethoxymethyl.

Etherified hydroxymethyl represents preferably lower alkoxymethyl, lower alkoxyalkoxymethyl such as methoxymethyloxymethyl, 2-oxa- or 2-thiacyclo- alkoxymethyl, particularly 2-tetrahydropyranyloxymethyl.

Halomethyl represents especially chloromethyl but may also be bromomethyl or iodomethyl.

An alkali metal represents preferably lithium but may also be potassium or sodium.

Groups convertible into $COR_1$ =carboxy include esters and amides, and such are not limited to ester and amide derivatives as defined herein for $COR_1$. Conversion to carboxy is generally accomplished by solvolysis, with acid or base.

Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with trifluoroacetic acid.

Acetyl may be oxidatively cleaved to carboxy by conversion first to trihaloacetyl, e.g. tribromo or triiodoacetyl, by treatment e.g. with sodium hypobromite, followed by cleavage with e.g. an aqueous base, such as sodium hydroxide.

Formyl, di(lower)-alkoxymethyl or alkylenedioxymethyl (formyl protected in the form of an acetal), e.g. the dimethyl acetal, are oxidized with e.g. silver nitrate, pyridinium dichromate or ozone to carboxy.

Vinyl may be converted to carboxy by ozonolysis to formyl, which is in turn oxidized to carboxy.

Hydrolysis of trialkoxymethyl to carboxy is advantageously carried out with inorganic acids such as hydrohalic or sulfuric acid. Hydrolysis of etherified hydroxymethyl to hydroxymethyl is preferably carried out with solutions of inorganic acids such as a hydrohalic acid. Hydroxymethyl is in turn oxidized to carboxy with an oxidizing agent such as pyridinium dichromate.

Halomethyl may also be converted to the corresponding carboxaldehydes with e.g. dimethylsulfoxide in the presence of triethylamine and silver tetrafluoroborate, or with chromium trioxide and pyridine in methylene chloride.

The conversion of cyano to lower alkoxycarbonyl is advantageously carried out by treatment first with a lower alkanol, e.g. anhydrous ethanol, in the presence of a strong acid, e.g. hydrochloric acid preferably at reflux temperature, followed by hydrolysis with water.

Furthermore, the conversion of cyano to carbamoyl is preferably carried out by treatment with an alkali metal hydroxide, e.g. dilute sodium hydroxide, and hydrogen peroxide, preferably at room temperature.

Esterified carboxy such as lower alkoxycarbonyl may be amidized with ammonia, mono- or di-(lower)alkylamines e.g. methylamine, dimethylamine in an inert solvent, e.g. a lower alkanol, such as butanol, to unsubstituted, mono- or di(lower) alkylcarbamoyl.

The compounds of the invention may thus also be converted to other compounds of the invention by e.g. functional group transformations well-known in the art.

For example, conversion of carboxylic acid esters and amides to carboxylic acids is advantageously carried out by hydrolysis with inorganic acids such as a hydrohalic or sulfuric acid or with aqueous alkalies, preferably alkali metal hydroxides such as lithium or sodium hydroxide.

Free carboxylic acids may be esterified with lower alkanols, such as ethanol, in the presence of a strong acid, e.g. sulfuric acid, or with diazo (lower) alkanes, e.g. diazomethane in a solvent such as ethyl ether, advantageously at room temperature, to give the corresponding lower alkyl esters.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower) alkylamines, in an inert solvent such as methylene chloride, preferably in the presence of a basic catalyst such as pyridine, to compounds wherein $COR_1$ represents unsubstituted, mono or di-(lower)- alkylcarbamoyl.

Phosphonic acid esters are converted to the corresponding phosphonic acids by treatment with acid, such as aqueous hydrochloric acid or hydrobromic acid in glacial acetic acid, or with bromotrimethylsilane according to J. Chem. Soc. Chem. Comm. 179, 739. Benzyl esters may be converted to the acids by hydrogenolysis.

Phosphonic acids are converted to esters, e.g. optionally substituted lower alkyl esters, e.g. by condensation with an optionally substituted lower alkyl halide preferably in a basic non-aqueous medium, such as in the presence of triethylamine.

The compounds of the invention wherein Y represents optionally substituted 2-carboxy-(tetrahydropyridinyl, tetrahydroquinolinyl, dihydroindolyl or dihydropyrrolyl) and derivatives thereof are converted to the corresponding piperidinyl, perhydroquinolinyl, perhydroindolyl or pyrrolidinyl compounds, respectively, e.g. by catalytic hydrogenation.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Mainly those starting materials should be used in said reactions, that lead to the formation of those compounds indicated above as being especially preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, such as antipodes, or as mixtures of optical isomers such as racemates or as mixtures of diastereoisomers or of geometric isomers. The aforesaid possible isomers or mixtures thereof are within the purview of this invention; certain particular isomers are preferred as indicated above.

Any resulting mixtures of diastereoisomers, mixtures of racemates can be separated on the basis of the physicochemical differences of the constituents, in known manner, into the pure isomers, diastereoisomers, racemates, or geometric isomers, for example by chromatography and/or fractional crystallization.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active free carboxylic or phosphonic acid antipodes can be liberated on acidification. The basic racemic products can likewise be resolved into the optical antipodes; e.g. by separation of the diastereoisomeric salts thereof, with an optically active acid, and liberating the optically active basic compound by treatment with a standard base. Racemic products of the invention can thus be resolved into their optical antipodes, e.g., by the fractional crystallization of d- or l-(tartrates, mandelates, camphorsulfonates) or of d- or l-(α-methylbenzylamine, cinchonidine, cinchonine, quinine, quinidine, ephedrine, dehydroabietylamine, brucine or strychnine) salts. The acidic compounds of the invention can also be resolved by separating diastereomeric ester or amide derivatives prepared from an optically active alcohol or amine, and regenerating the reduced optically active compound. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation, or an alkylene oxide such as propylene oxide. A compound of the invention with a free carboxylic or phosphonic acid group can thus also be converted into the corresponding metal or ammonium salts. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parental administration to mammals, including man, for blockade of the N-methyl-D-aspartate excitatory amino acid receptor and for the treatment of diseases responsive to blockade of the N-methyl-D-aspartate excitatory amino acid receptor, such as cerebral ischemia, convulsive disorders and anxiety, comprising an effective amount of a pharmacologically active compound of the invention, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parental application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and/or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The invention also relates to a method of blocking the N-methyl-D-aspartate excitatory amino acid receptor in mammals, and to a method of treatment of disorders in mammals, e.g. such responsive to blockade of the N-methyl-D-aspartate excitatory amino acid receptor, such as cerebral ischemia, convulsive disorders and anxiety, using an effective amount of a compound of the invention as a pharmacologically active substance, preferably in the form of above-cited pharmaceutical compositions.

A particular embodiment thereof relates to a method of treating cerebral ischemia and of inhibiting brain damage resulting from cerebral ischemia (in a stroke) in mammals which comprises the administration to a mammal in need thereof of an effective amount of an N-methyl-D-aspartate blocking compound of the invention or of a pharmaceutical composition comprising a said compound.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

A mixture of 1.19 g of 4-(diethylphosphonomethyl)-2pyridinecarboxamide and 0.75 g of platinum oxide in 30 ml of acetic acid is hydrogenated at 3 atmospheric pressure for 6 hours at room temperature. The reaction mixture is filtered and the solvent is removed in vacuo. The residue is dissolved in methylene chloride and washed with a small volume of saturated sodium bicarbonate solution. After drying over magnesium sulfate, a methylene chloride solution of a 2:1 mixture of cis and trans 4-(diethylphosphonomethyl)-2-piperidinecarboxamide is obtained. After 3 days at room temperature this mixture isomerizes to the more stable cis isomer. Removal of the solvent in vacuo affords cis-4-(diethylphosphonomethyl)-2-piperidinecarboxamide as an oil, which is converted to the hydrochloride salt, melting at 155°–158°.

The starting material is prepared as follows: A mixture of 2.2 g of 4-(diethylphosphonomethyl)pyridine [Roczniki Chem. 38, (4), 625 (1964); Chem. Abst. 61, 10703], 2.2 g of m-chloroperbenzoic acid and 30 ml of chloroform is stirred at room temperature for 16 hours. The solvent is removed in vacuo and water is added. After washing the aqueous layer with ether, the water is removed in vacuo to afford 4-(diethylphosphonomethyl)pyridine-N-oxide.

A mixture of 1.2 g of 4-(diethylphosphonomethyl)-pyridine-N-oxide, 1.35 ml of triethylamine and 2.6 ml of trimethylsilylcyanide is heated at 90° for 1 hour. The volatiles are removed in vacuo and the residue is dissolved in ethyl acetate and washed with a small volume of aqueous sodium bicarbonate. After drying over magnesium sulfate the solvent is removed in vacuo to afford 2-cyano-4-(diethylphosphonomethyl)pyridine as an oil.

A mixture of 1.10 g of 2-cyano-4-(diethylphosphonomethyl)pyridine and 4.5 ml of concentrated sulfuric acid is heated at 90° for 5 minutes. The reaction mixture is poured onto ice and neutralized with 10% sodium hydroxide. The resulting precipitate is collected to afford 4-(di-ethylphosphonomethyl)-2-pyridinecarboxamide melting at 140°–142°.

EXAMPLE 2

A solution of 3.0 g of cis-4-(diethylphosphonomethyl)-2-piperidinecarboxamide in 90 ml of 20% hydrochloric acid is heated under reflux with stirring for 16 hours. After removal of the solvent, the residue is crystallized from ethyl acetate/ethanol to afford cis-4-phosphonomethyl-2-piperidinecarboxylic acid hydrochloride, melting at 284°–285° (dec).

EXAMPLE 3

A mixture of 330 mg of 4-phosphonomethyl-2-pyridinecarboxylic acid, 150 mg of platinum oxide, 20 ml of acetic acid and 100 ml of water is hydrogenated at 3 atmospheres pressure at room temperature for 20 hours. The solvent is removed in vacuo to afford a 2:1 mixture of cis and trans 4-phosphonomethyl-2-piperidinecarboxylic acid. The residue is dissolved in aqueous hydrochloric acid and the solvent removed in vacuo to afford a 2:1 mixture of cis and trans 4-phosphonomethyl-2-piperidinecarboxylic acid hydrochloride melting at 145° (dec).

The starting material was prepared as follows: A mixture of 350 mg of 2-cyano-4-diethylphosphonomethylpyridine and 10 ml of 20% hydrochloric acid is refluxed for 16 hours. After removal of the solvent in vacuo the residue is triturated with 95% ethanol to afford 4-phosphonomethyl-2-pyridinecarboxylic acid melting at 265°–268° (dec).

EXAMPLE 4

Prepared essentially according to the procedures described in the previous examples are:
a) cis and trans 5-phosphonomethyl-2-piperidinecarboxylic acid hydrochloride, m.p. above 250°;
b) cis and trans 3-phosphonomethyl-2-piperidinecarboxylic acid hydrochloride, m.p. above 250°;
c) cis 3-(2-phosphonoethyl)-2-piperidinecarboxylic acid, m.p. 160°–190° dec.
d) cis-5-(2-phosphonoethyl)-2-piperidinecarboxylic acid hydrochloride, m.p. 125° dec.
e) cis 4-(2-phosphonoethyl)-2-piperidinecarboxylic acid;
f) cis 4-(3-phosphonopropyl)-2-piperidinecarboxylic acid, m.p. 287° dec.
g) cis 4-(1-methyl-1-phosphonoethyl)-2-piperidinecarboxylic acid hydrochloride, m.p. 250° (dec).

h) cis 4-(1-phosphonoethyl)-2-piperidinecarboxylic acid, m.p. 220° dec, e.g. via 4-(1-phosphonoethyl)-2-pyridine carboxylic acid, m.p. 264°-265° dec.

i) 5-(3-phosphonopropyl)-2-piperidinecarboxylic acid e.g. via 5-(3-phosphonopropyl)-2-pyridinecarboxylic acid hydrochloride, m.p. 210°-220° dec.

j) cis 3-(3-phosphonopropyl)-2-piperidinecarboxylic acid, via 3-(3-phosphonopropyl)-2-pyridinecarboxylic acid, m.p. 230°-235° dec.

k) 3-methyl-4-phosphonomethyl-2-piperidinecarboxylic acid, m.p. 325° dec., starting from 3-methyl-4-chloromethylpyridine via reduction of 3-methyl-4-phosphonomethylpyridinecarboxylic acid.

l) cis-6-methyl-4-phosphonomethyl-2-piperidinecarboxylic acid, m.p. 260°-265°, starting from 2-methyl-4-chloromethylpyridine.

m) cis-5-methyl-4-phosphonomethyl-2-piperidinecarboxylic acid, m.p. above 250°, starting from 3-methyl-4-chloromethylpyridine via reduction of 5-methyl-4-phosphonomethyl-2-pyridinecarboxylic acid, m.p. 295° dec.

Certain starting materials are prepared as follows:

1. Treatment of 3-(diethylphosphonomethyl)pyridine (Biochemistry 19, 3400) with m-chloroperbenzoic acid followed by trimethylsilyl cyanide gives both 3-(diethylphosphonomethyl)-2-cyanopyridine and 5-(diethylphosphonomethyl)-2-cyanopyridine, the starting materials for compounds under a) and b).

2. Similarly, 3-(2-diethylphosphonoethyl)pyridine (Biochemistry 19, 3400) is converted to the corresponding starting materials for compounds under c) and d); 4-(2-diethylphosphonoethyl)pyridine (Chem. Abstracts 89, 35665) is converted to 4-(2-diethylphosphonoethyl)-2-cyanopyridine, the starting material for compound under e).

3. Reaction of 3-(4-pyridinyl)propyl chloride with diethyl phosphite (diethyl phosphonate) and sodium hydride in toluene yields 4-(3-diethylphosphonopropyl)pyridine which is converted according to the procedure described hereinabove to 4-(3-diethylphosphonopropyl)-2-cyanopyridine, the starting material for compound under f).

4. A mixture of 1.0 g of 4-(diethylphosphonomethyl)-pyridine and 0.5 g of 50% sodium hydride in 4 ml of dimethylformamide and 16 ml of tetrahydrofuran is heated under reflux for 30 minutes. Methyl iodide (0.52 ml) is added and heating under reflux is continued for 30 minutes. The reaction mixture is evaporated to dryness and the residue is chromatographed on silica gel with methanol/methylene chloride (1:10) as the eluant to give 4-(1-methyl-1-diethylphosphonoethyl)-pyridine which is converted to 2-cyano-4-(1-methyl-1-diethylphosphonoethyl)-pyridine, the starting material for compound under g).

5. Similarly treatment of 4-(diethylphosphonomethyl)pyridine as above with 1 mole equivalent of methyl iodine yields 4-(1-diethylphosphonoethyl)pyridine, the starting material for compound under h).

EXAMPLE 5 a) A solution of 370 mg of cis-4-phosphonomethyl-2-piperidinecarboxylic acid in 15 ml of saturated ethanolic hydrochloric acid is heated under reflux for 16 hours. The solvent is removed in vacuo. A solution of the residue in ethanol is treated with 0.21 ml of propylene oxide and evaporated to dryness to yield cis-4-phosphonomethyl-2-piperidinecarboxylic acid ethyl ester, m.p. 230°-235° dec.

Similarly prepared are:

b) cis-4-phosphonomethyl-2-piperidinecarboxylic acid methyl ester, m.p. 198°-200°;

c) cis-4-phosphonomethyl-2-piperidinecarboxylic acid n-butyl ester, m.p. 241°-244°;

d) cis-4-(3-phosphonopropyl-2-piperidinecarboxylic acid ethyl ester, m.p. 197°-202°;

e) cis-4-phosphonomethyl-2-piperidinecarboxylic acid n-propyl ester, m.p. 245°-249°;

f) cis-4-phosphonomethyl-2-piperidinecarboxylic acid isobutyl ester, m.p. 254°-259°.

EXAMPLE 6 a) A solution of 278 mg of cis-4-diethylphosphonomethyl-2-piperidinecarboxamide in 5 ml of methylene chloride to which is added 0.43 ml of trimethylsilyl iodide is stirred at room temperature for 16 hours. The mixture is evaporated to dryness, the residue is dissolved in water, and the solution is evaporated to dryness. A solution of the resulting solid in ethanol is treated with 0.21 ml of propylene oxide to yield cis-4-phosphonomethyl-2-piperidinecarboxamide, m.p. 295°-298° dec.

EXAMPLE 7 a) To a solution of 200 mg of cis-4-phosphonomethyl-2-piperidinecarboxylic acid, 96 mg of sodium carbonate in 5 ml of water and 2.31 ml of 1N aqueous sodium hydroxide is added 119 mg of benzoyl chloride. The reaction mixture is stirred at room temperature for 16 hours and the solvent is removed in vacuo. The residue is dissolved in ethanol, the solution is filtered and evaporated to dryness. Crystallization from ethanol/ethyl acetate affords cis-1-benzoyl-4-phosphonomethyl-2-piperidinecarboxylic acid, m.p. 135°-145° dec.

b) Similarly prepared is cis-1-benzyloxycarbonyl-4-phosphonomethyl-2-piperidinecarboxylic acid methyl ester.

c) Similarly prepared is cis 1-(3-phenylpropionyl)-4-phosphonomethyl-2-piperidinecarboxamide, m.p. 95°-100°, via cis 4-phosphonomethyl-2-piperidinecarboxamide.

EXAMPLE 8

A mixture of 357 mg of cis-1-benzyloxycarbonyl-4-phosphonomethyl-2-piperdinecarboxylic acid, 550 mg of diisopropylethylamine and 600 mg of chloromethyl pivalate in 2 ml of dimethylformamide is heated at 80° for 2 hours. The reaction mixture is evaporated to dryness at 70°/0.1 mm Hg. The residue is dissolved in ethyl acetate, the solution is washed with water and evaporated to dryness to yield cis-1-benzyloxycarbonyl-4-[di(pivaloyloxymethyl)phosphonomethyl]-2-piperidinecarboxylic acid pivaloyloxymethyl ester (after chromatography on silica gel using ether/methylene dichloride as the eluant). The product is dissolved in 40 ml of ethanol and hydrogenated in the presence of 10% palladium on charcoal to yield cis-4-[di-(pivaloyloxymethyl)-phosphonomethyl]-2-piperidinecarboxylic acid pivaloyloxymethyl ester.

The starting material is prepared by treatment of cis-4-phosphonomethyl-2-piperidinecarboxylic acid with benzyl chloroformate under standard amino acid acylation conditions, e.g. as described in Example 7.

EXAMPLE 9 a) A mixture of 500 mg of 4-(diethylphosphonomethyl)-quinoline-2-carboxamide and 1 g of 10% palladium on charcoal in 75 ml of methanol is hydrogenated at 3 atmospheres pressure for 24 hours, filtered and evaporated to dryness. Chromatography on silica gel using methanol/methylene chloride (1:10) as eluant yields cis-4-(diethylphosphonomethyl)-1,2,3,4-tetrahydroquinoline-2-carboxamide.

The starting material is prepared as follows:

To a stirred solution of 10 g of 4-quinolinecarboxaldehyde in 400 ml of absolute ethanol at room temperature is added 2.4 g of sodium borohydride. After 45 minutes, 20 ml of water is added and the reaction mixture is stirred for an additional 20 minutes. Acetic acid (20 ml) is added slowly. The reaction mixture is evaporated to a small volume and partitioned between water and methylene chloride. The organic layer is washed with saturated potassium carbonate, saturated sodium chloride solution, dried over sodium sulfate and evaporated to dryness. The residue is purified by chromatography on silica gel using methanol/methylene chloride (1:10) as eluant to yield 4-hydroxymethylquinoline; $R_f=0.59$.

A solution of methanesulfonyl chloride (4.84 ml) in 20 ml of methylene chloride is slowly added over 20 minutes to a solution of 8.29 g of 4-hydroxymethylquinoline and 11 ml of triethylamine in 200 ml of methylene chloride at 0°. After completion of the reaction at room temperature, the reaction mixture is partitioned between methylene chloride and saturated potassium carbonate solution. The organic layer is dried over sodium sulfate and evaporated to dryness to yield 4-(methanesulfonyloxymethyl)quinoline as an oil.

To a solution of 1.62 g of sodium hydride (from 3.24 g of a 50% sodium hydride dispersion in mineral oil) in 100 ml of toluene is added dropwise a solution of 8 ml of diethyl phosphite in 20 ml of toluene. The reaction mixture is heated to 80°, a solution of the above obtained 4-(methanesulfonyloxymethyl)-quinoline in 90 ml of toluene and 10 ml of methylene chloride is added. After 20 minutes a second portion of 1.2 g of sodium hydride is added and the reaction mixture is stirred for an additional 10 minutes. The reaction mixture is then evaporated to dryness, the product is partitioned between water and ethyl acetate. The ethyl acetate extract is washed with saturated sodium chloride solution, dried over sodium sulfate and evaporated to dryness. The residue is chromatographed on silica gel using methanol/methylene chloride (5:95) as eluant to yield 4-(diethylphosphonomethyl)quinoline; $R_f=0.3$.

To a solution of 5.7 g of 4-(diethylphosphonomethyl)-quinoline in 100 ml of methylene chloride at room temperature is added 3.2 g of m-chloroperbenzoic acid. After reacting for 45 minutes, an additional 1.5 g portion of m-chloroperbenzoic acid is added, and the reaction mixture is stirred for one hour. The reaction mixture is washed with saturated potassium carbonate solution, dried over sodium sulfate and evaporated to dryness to give 4-(diethylphosphonomethyl)-quinoline-N-oxide.

A mixture of 5.9 g of 4-(diethylphosphonomethyl)-quinoline-N-oxide, 15 ml of trimethylsilyl cyanide and 7 ml of triethylamine is heated at 80° for 1 hour and evaporated to dryness. The residue is purified by chromatography on silica gel using methanol/methylene chloride (5:95) as eluant to yield 4-(diethylphosphonomethyl)-2-cyanoquinoline as an oil.

A solution of 5.9 g of 4-(diethylphosphonomethyl)-2-cyanoquinoline in 24 ml of concentrated sulfuric acid is heated at 80° for 5 minutes, cooled to 0° and added slowly to an ice-cooled mixture of 50 g of sodium carbonate in 50 ml of water and 100 ml of methylene chloride. The organic layer is separated, dried over sodium sulfate and evaporated to dryness to yield 4-(diethylphosphonomethyl)-quinoline-2-carboxamide.

b) Similarly prepared is cis-4-(3-diethylphosphonopropyl)-1,2,3,4-tetrahydroquinoline-2-carboxamide.

EXAMPLE 10 a) A solution of 220 mg of cis-4-(diethylphosphonomethyl)-1,2,3,4-tetrahydroquinoline-2-carboxamide in 50 ml of 6N aqueous hydrochloric acid is heated under reflux for 14 hours, and evaporated to dryness. The residue is dried under high vacuum at 100° for 48 hours to yield cis-4-phosphonomethyl-1,2,3,4-tetrahydroquinoline-2-carboxylic acid, m.p. 171°–173°.

b) Similarly prepared is cis-4-(3-phosphonopropyl)-1,2,3,4-tetrahydroquinoline-2-carboxylic acid hydrochloride.

EXAMPLE 11 a) Treatment of cis-4-phosphonomethyl-1,2,3,4-tetrahydroquinoline-2-carboxylic acid first with benzyl chloroformate and then with chloromethyl pivalate under conditions essentially as described in example 8, including the hydrogenolysis, yields 4-[di-(pivaloyloxymethyl)phosphonomethyl]-1,2,3,4-tetrahydroquinoline-2-carboxylic acid pivaloyloxymethyl ester.

b) Treatment of cis-4-phosphonomethyl-1,2,3,4-tetrahydroquinoline-2-carboxylic acid with ethanolic hydrochloric acid under conditions essentially as described in Example 5 yields cis-4-phosphonomethyl-1,2,3,4-tetrahydroquinoline-2-carboxylic acid ethyl ester.

EXAMPLE 12

A mixture of 400 mg of 4-phosphonomethylquinoline-2-carboxylic acid hydrochloride, 150 mg of platinum oxide, 20 ml of acetic acid and 100 ml of water is hydrogenated at 3 atmospheres pressure at room temperature for 20 hours to afford cis-4-phosphonomethyl-perhydroquinoline-2-carboxylic acid; HCl salt; m.p. 230°–250° dec.

The starting material is prepared as follows:

A solution of 4-(diethylphosphonomethyl)quinoline-2-carboxamide with 6N hydrochloric acid is heated under reflux overnight to yield 4-phosphonomethyl-quinoline-2-carboxylic acid hydrochloride, m.p. 218°–221°.

EXAMPLE 13

A mixture of 2.0 g of 4-(diethylphosphonomethylidene)-N-t-butoxycarbonylpyrrolidine-2-carboxylic acid methyl and ethyl ester, and 800 mg of 10% palladium on charcoal catalyst in 30 ml of ethanol is hydrogenated at 3 atmospheres pressure and room temperature for 18 hours. The reaction mixture is filtered free of catalyst, the catalyst is washed with methylene chloride, the combined filtrate is evaporated to dryness to yield a mixture of N-t-butoxycarbonyl-4-diethylphosphonomethylpyrrolidine-2-carboxylic acid methyl and ethyl esters.

The above product is treated with 10 ml trifluoroacetic acid for 5 minutes, the trifluroacetic acid is removed under vacuum. A solution of the residue in 30 ml of 6N hydrochloric acid is heated under reflux for 6 hours and evaporated to dryness. A solution of the residue in 15 ml ethanol is treated with 1 ml of propylene oxide. The resulting precipitate is filtered off to yield 4-phosphonomethylpyrrolidine-2-carboxylic acid (4-phosphonomethylproline); NMR (D$_2$O): 4.53, 3.82, 2.88, 2.80, 2.0 ppm; product is mixture of cis and trans compounds (about 9:1).

The starting material is prepared as follows:

A mixture of 10.0 g of 4-hydroxyproline, 13 ml of 6N sodium hydroxide solution and 19.0 g of di-t-butyl dicarbonate is stirred vigorously at room temperature for 24 hours. Concentrated hydrochloric acid (6.5 ml) is added and the reaction mixture is extracted with 30 ml of chloroform. The chloroform is discarded, the oil is separated from the aqueous layer to give N-t-butoxycarbonyl-4-hydroxyproline. A solution thereof in 70 ml of methanol is treated with ethereal diazomethane (prepared from 20 g of N-methyl-N-nitrosourea, 60 ml of 40% aqueous potassium hydroxide and 200 ml of ether) to give N-t-butoxycarbonyl-4-hydroxyproline methyl ester.

A mixture of 12.7 g of N-t-butoxycarbonyl-4-hydroxyproline methyl ester and 44.7 g of pyridinium chlorochromate in 150 ml of methylene chloride is stirred at room temperature for 30 hours, diluted with 200 ml of ether and filtered through Florisil washing with ether (500 ml). The solution is evaporated to dryness, the residue is purified by flash chromatography on silica gel using ethyl acetate/hexane (40:60) as eluant to give N-t-butoxycarbonyl-4-oxoproline methyl ester.

A solution of 2.28 M n-butyl lithium (4.6 ml) is added at $-78°$ to a solution of 3.07 g of bis-(diethylphosphono)methane in 50 ml of dry tetrahydrofuran. After 5 minutes, a solution of 2.5 g of N-t-butoxycarbonyl-4-oxoproline methyl ester is added. The reaction mixture is heated under reflux for 20 hours. The volume is reduced to 20 ml and the product is partitioned between methylene chloride and 2N hydrochloric acid. The methylene chloride extract is dried and evaporated to dryness and the residue is purified by flash chromatography on silica gel eluting with methylene chloride/methanol (95:5) to obtain a mixture of 4-(diethylphosphonomethylidene)-N-t-butoxycarbonylpyrrolidine-2-carboxylic acid methyl and ethyl esters.

EXAMPLE 14

Preparation of an injectable formulation containing 10 mg of the active ingredient per 5 ml of solution:

| Formula | |
| --- | --- |
| cis-4-phosphonomethyl-2-piperidine-carboxylic acid hydrochloride | 10.0 g |
| Propylparaben | 0.5 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 15

A solution of 2.0 g of cis-1-benzyloxycarbonyl-4-phosphonomethyl-2-piperidinecarboxylic acid in 10 ml of methylene chloride is treated with ethereal diazomethane until a persistent yellow color is obtained. After removal of solvent the triester is heated at 50° in 10 ml of tetrahydrofuran and 10 ml of 1N sodium hydroxide. After acidification the product is extracted with ether, the organic layer dried and evaporated to yield cis-1-benzyloxycarbonyl-4-dimethylphosphonomethyl-2-piperidinecarboxylic acid.

EXAMPLE 16

A solution of 1.0 g of cis-1-benzyloxycarbonyl-4-dimethylphosphonomethyl-2-piperidinecarboxylic acid in 30 ml of ethanol is hydrogenated at 3 atmospheres pressure over 500 mg of 10% palladium on carbon catalyst in 30 ml of ethanol. Filtration and removal of solvent affords cis-4-dimethylphosphonomethyl-2-piperidine-carboxylic acid as an amorphous solid.

EXAMPLE 17

A solution of 3.38 g of cis-1-benzyloxycarbonyl-4-dimethylphosphonomethyl-2-piperidinecarboxylic acid in 35 ml of methylene chloride is treated with 1.42 g of 1,1'-carbonyldiimidazole and 1.3 g of (+)-alpha-methylbenzylamine. After stirring for 16 hours, the reaction mixture is washed with 1N hydrochloric acid and saturated sodium bicarbonate solution, dried, and the solvent removed. Separation of the resulting diastereomers by high pressure liquid chromatography (HPLC) using a reverse phase $C_{18}$ column and acetonitrile/water (2:3) as eluant affords the two diastereomers of cis-1-benzyloxycarbonyl-4-dimethylphosphonomethyl-2-piperidine-(N-1-phenylethyl)carboxamide.

Hydrogenation of the first eluted diastereomer in ethanol with palladium on charcoal catalyst for 4 hours at 3 atmospheres pressure affords the corresponding cis-4-dimethylphosphonomethyl-2-piperidine-(N-1-phenylethyl)-carboxamide. Treatment with 6N hydrochloric acid under reflux for 24 hours affords (−)-cis-4-phosphonomethyl-2-piperidinecarboxylic acid, $[\alpha]_D^{25} = -5.93°$ (H$_2$O), the pharmacologically more active enantiomer of the compound of Example 2.

The corresponding (+)-cis-4-phosphonomethyl-2-piperidinecarboxylic acid, the less active enantiomer, is similarly obtained.

EXAMPLE 18

A mixture of 600 mg of cis-1-benzyloxycarbonyl-4-dimethylphosphonomethyl-2-piperidinecarboxylic acid methyl ester in 10 ml of methylene chloride is treated with 538 mg of trimethylsilyl iodide at room temperature to yield cis 1-benzyloxycarbonyl-4-phosphonomethyl-2-piperidinecarboxylic acid methyl ester as an oil.

EXAMPLE 19

A mixture of 500 mg of cis-4-diethylphosphonomethyl-2-piperidinecarboxamide, 3 ml of 37% aqueous formaldehyde, 50 ml of methanol and 500 mg of 10% palladium on carbon catalyst is hydrogenated at 3 atmospheres pressure for 16 hours. The solvent is removed and the residue chromatographed on silica gel with 10% methanol/methylene chloride as the eluant to afford cis-1-methyl-4-diethylphosphonomethyl-2-piperidinecarboxamide. This product is refluxed for 16 hours in 6N hydrochloric acid followed by treatment with propylene oxide to yield cis 1-methyl-4-phosphonomethyl-2-piperidinecarboxylic acid, m.p. 256°–260°.

EXAMPLE 20

A solution of 1.0 g of cis 4-diethylphosphonomethyl-2-piperidinecarboxylic acid ethyl ester is reacted with 552 mg of N-t-butoxycarbonylglycine in the presence of N,N'-dicyclohexyl-carbodiimide in 10 ml of methylene chloride of room temperature for 16 hours to yield cis 1-[alpha-(t-butoxycarbonylamino)acetyl]-4-diethylphosphonomethyl-2-piperidinecarboxylic acid ethyl ester as an oil. Treatment with trimethylsilyl iodide yields cis 1-(alpha-aminoacetyl)-4-phosphonomethyl-2-piperidine
carboxylic acid ethyl ester, m.p. 150°–155° dec.

EXAMPLE 21 a) Methyl N-t-butoxycarbonyl-4-(diethylphosphonoethyl)pyrrolidine-2-carboxylate (0.45 g) is hydrolyzed as described in Example 13 to yield cis 4-(2-phosphonoethyl)pyrrolidine-2-carboxylic acid; NMR ($D_2O$): 4.22, 3.45, 2.95, 2.54, 2.4 ppm (1H each).

The starting material is prepared as follows:

To a suspension of 3.44 g of benzyloxycarbonylmethyltriphenylphosphonium bromide in 20 ml of tetrahydrofuran is added 10 ml 0.65 M potassium hexamethyldisilazide solution in toluene followed by 1.5 g N-t-butoxycarbonyl-4-oxoproline methyl ester in 4 ml of tetrahydrofuran. After refluxing for 72 hours the solvent is evaporated and the residue flash chromatrographed with ethyl acetate/hexane (20:80) to afford a mixture of cis and trans (mostly cis) methyl N-t-butoxycarbonyl-4-(2-oxo-2-benzyloxyethylidene)-pyrrolidine-2-carboxylate.

A solution of 0.58 g of the above product in 15 ml of methanol is hydrogenated at 3 atmospheres pressure for 3 hours in the presence of 400 mg of 10% Pd/C. The reaction mixture is filtered through Celite, the solvent evaporated and the residue flash chromatographed with methanol/methylene chloride (10:90) to afford cis methyl N-t-butoxycarbonyl-4-(carboxymethyl)pyrrolidine-2-carboxylate.

To 0.67 g of cis methyl N-t-butoxycarbonyl-4-(carboxymethyl)-pyrrolidine-2-carboxylate in 1 ml THF is added at 0° 3.5 ml of borane (1M) in THF. After stirring 0.5 hour, 1 ml of water is added, the solvent is evaporated and the residue is flash chromatographed with ethyl acetate/hexane (75:25) to afford cis methyl N-t-butoxycarbonyl-4-(2-hydroxyethyl)-pyrrolidine-2-carboxylate.

To a solution of 0.58 g of cis methyl N-t-butoxycarbonyl-4-(2-hydroxyethyl)pyrrolidine-2-carboxylate in 6 ml methylene chloride is added at 0° 0.577 g triphenylphosphine followed by 0.388 g N-bromosuccinimide. After stirring 0.5 hour, the solvent is evaporated and the residue flash chromatographed using ethyl acetate/hexane (35:65) to afford cis methyl N-t-butoxycarbonyl-4-(2-bromoethyl)-pyrrolidine-2-carboxylate.

A mixture of 0.60 g of cis methyl N-t-butoxycarbonyl-4-(2-bromoethyl)pyrrolidine-2-carboxylate and 3 ml triethyl phosphite is refluxed for 2 hours. The excess triethyl phosphite is distilled off under vacuum and the residue is flash chromatographed with methylene chloride/methanol (95:5) to afford cis methyl N-t-butoxycarbonyl-4-(2-di-ethylphosphonoethyl)pyrrolidine-2-carboxylate.

b) Similarly obtained is (+)-cis-4-(2-phosphonoethyl)pyrrolidine-2-carboxylic acid, $[\alpha]_D^{25} = +23.7°$, starting with the D-proline derivative.

c) Similarly prepared is cis 3-(2-phosphonoethyl)pyrrolidine-2-carboxylic acid; NMR ($D_2O$): 4.34, 3.57, 3.35, 2.67 and 2.27 (1H each), 1.79 (4H), 1.52 (1H).

d) Similarly prepared is trans 3-(2-phosphonoethyl)pyrrolidine-2-carboxylic acid; NMR ($D_2O$) 3.88, 3.44, 3.31, 2.47, 2.24 (1H each), 1.71 (4H), 1.45 (1H).

The starting material for the trans product d) is prepared as follows:

A solution of 1.25 g of ethyl 3-(2-oxo-2-benzyloxyethylidene)-1-ethoxycarbonylpyrrolidine-2-carboxylate (obtained according to the procedure described under a) in 10 ml of anhydrous ethanol containing one equivalent of lithium ethoxide is heated under reflux for seven days. One equivalent of 1N hydrochloric acid is added to the cooled solution, which is then concentrated, diluted with 20 ml water and extracted with three 20 ml portions at methylene chloride. The extracts are dried over sodium sulfate, filtered and concentrated. The residue is chromatographed under high pressure eluting with ethyl acetate/hexane (5:95) to afford trans ethyl 3-(2-oxo-2-benzyloxyethylidene)-1-ethoxycarbonylpyrrolidine-2-carboxylate (in addition to approximately an equal amount at the cis isomer) which is converted to trans ethyl 1-ethoxycarbonyl-3-(diethylphosphonoethyl)-pyrrolidine-2-carboxylate essentially as described under a).

EXAMPLE 22 a) A stirred solution of 5.3 ml of bis-(diethylphosphono)methane in 30 ml of anhydrous tetrahydrofuran (THF) under nitrogen is cooled to −78° and 8.5 ml of 2.5M butyl lithium is added dropwise. After stirring 5 minutes a solution of 4.64 g of ethyl 1-ethoxycarbonyl-3-oxopyrrolidine-2-carboxylate [J. Am. Chem. Soc. 86, 5297 (1964)]in 30 ml dry THF is added dropwise rapidly. The solution is heated at reflux for 18 hours, cooled to room temperature and concentrated; 40 ml of 1N hydrochloric acid is added and the mixture is extracted with 100 ml of methylene chloride. The organic fraction is washed with 25 ml water, dried over $Na_2SO_4$, filtered and concentrated. Purification by flash chromatography using ethyl acetate as solvent yields ethyl 1-ethoxycarbonyl-3-(diethylphosphonomethyl)-2,5-dihydropyrrole-2-carboxylate.

EXAMPLE 23

A solution of 2.75 g of ethyl 1-ethoxycarbonyl-3-(diethylphosphonomethyl)-2,5-dihydropyrrole-2-carboxylate in 35 ml ethyl alcohol and 1.5 g 10% Pd/C is hydrogenated at 3 atmospheres pressure to yield cis and trans ethyl 1-ethoxycarbonyl-3-(diethylphosphonomethyl)-pyrrolidine-2-carboxylate.

EXAMPLE 24 a) A solution of 2.7 g of cis and trans ethyl 1-ethoxycarbonyl-3-(diethylphosphonomethyl)pyrrolidine-2-carboxylate is heated under reflux with 6N hydrochloric acid for 6 hours to yield 3-(phosphonomethyl)pyrrolidine-2-carboxylic acid hydrochloride; NMR ($D_2O$): 4.78, 4.40, 3.95, 3.83, 3.72, 3.20, 3.01, 2.78, 2.69 ppm.

b) Similarly hydrolysis of ethyl 1-ethoxycarbonyl-3-(diethylphosphonomethyl)-2,5-dihydropyrrole-2-carboxylate affords 3-(phosphonomethyl)-2,5-dihydropyrrole-2-carboxylic acid hydrochloride which on treatment with propylene oxide yields the free amino acid, m.p. 215° dec.

EXAMPLE 25

Ethyl 4-[1-(3-diethylphosphonoprop-2-enyl)]-1-tert-butoxycarbonylpiperidine-2-carboxylate is hydrolyzed with 6N hydrochloric acid to yield 4-[1-(3-phosphonoprop-2-enyl)]piperidine-2-carboxylic acid.

The starting material is prepared as follows:

4-(2-hydroxyethyl)-pyridine is oxidized to 4-(2-hydroxyethyl)-pyridine-N-oxide which is in turn treated with trimethylsilyl cyanide to yield 4-(2-hydroxyethyl)-2-cyanopyridine which is converted to ethyl 4-(2-hydroxyethyl)-2-pyridine carboxylate and then hydrogenated to yield ethyl 4-(2-hydroxyethyl)-piperidine-2-carboxylate.

A solution of 2.01 g of ethyl 4-(2-hydroxyethyl)-piperidine-2-carboxylate in 5 ml methylene chloride is added to a solution of 2.20 g of di-tert-butyl dicarbonate in 10 ml methylene chloride. After standing for 10 minutes the solvent is evaporated and the residue is flash chromatographed with hexane: ethyl acetate (50:50) to afford ethyl 4-(2-hydroxyethyl)-1-tert-butoxycarbonyl-piperidine-2-carboxylate.

To a solution of 1.56 g of dimethyl sulfoxide in 10 ml methylene chloride is added 2.2 g of oxalyl chloride at $-78°$. After 20 minutes 2.4 g of ethyl(2-hydroxyethyl)-1-tert-butoxycarbonyl-piperidine-2-carboxylate in 5 ml methylene chloride is added. The reaction is stirred for one hour and 2.2 g of triethylamine is added. The ice bath is removed, the solvent evaporated and the residue is flash chromatographed with hexane: ethyl acetate (70:30) to afford ethyl 1-tert-butoxycarbonylpiperidine-2-carboxylate-4-acetaldehyde.

At $-78°$, 2.73 ml n-butyllithium (2.5) is added to 2.02 g bis(diethylphosphono)-methane in 20 ml anhydrous tetrahydrofuran. After 5 minutes 2.08 g of ethyl 1-tert-butoxycarbonylpiperidine-2-carboxylate-4-acetaldehyde in 5 ml tetrahydrofuran is added. The mixture is then refluxed for 16 hours. The cooled reaction mixture is concentrated and flash chromatographed (95:5 methelene chloride:methanol) to yield ethyl 4-[1-(3-diethylphosphonoprop-2-enyl)]-1-tert-butoxycarbonyl-piperidine-2-carboxylate.

EXAMPLE 26

The following compounds can be prepared according to methods generally illustrated in the previous examples:

(a) trans 3-[1-(4-phosphonobut-3-enyl)]-pyrrolidine-2-carboxylic acid;
(b) trans 3-[1-(4-phosphonobut-2-enyl)]-pyrrolidine-2-carboxylic acid;
(c) trans 3-[1-(4-phosphonobutyl]-pyrrolidine-2-carboxylic acid (by hydrogenation of double bond in compound of example (a) above).

The starting material for compound (a) can be prepared as follows:

Trans ethyl N-ethoxycarbonyl-pyrrolidine-2-carboxylate-3-acetaldehyde is condensed with $(C_6H_5)_3P=CHOCH_3$ under conditions of the Wittig reaction to afford trans ethyl N-ethoxycarbonylpyrrolidine-2-carboxylate-3-propionaldehyde. Condensation with bis-(diethylphosphono)methane under conditions described herein (e.g. example 25) yields trans ethyl 3-[1-(4-diethylphosphonobut-3-enyl)]-pyrrolidine-2-carboxylate.

The starting material for compound (b) can be prepared as follows:

The alcohol, trans ethyl N-ethoxycarbonyl-3-(2-hydroxyethyl)-pyrrolidine-2-carboxylate is oxidized to the aldehyde, trans ethyl N-ethoxycarbonylpyrrolidine-2-carboxylate-3-acetaldehyde, which is condensed with triphenylphosphoranylideneacetaldehyde under conditions of the Wittig reaction; the resulting $\alpha,\beta$-unsaturated $C_4$-aldehyde is reduced to the corresponding alcohol which is converted to the bromide. Condensation with triethyl phosphite yields ethyl 3-[1-(4-diethylphosphonobut-(2-enyl)]-pyrrolidine-2-carboxylate.

(d) 4-[1-(3-Phosphonoprop-1-enyl)]piperidine-2-carboxylic acid can be similarly prepared using ethyl 4-hydroxymethyl-N-ethoxycarbonylpiperidine-2-carboxylate as intermediate.

EXAMPLE 27 a) A mixture of 348 mg of 3-phosphonopyridine-2-carboxylic acid hydrochloride and 100 mg of Adams catalyst in dilute aqueous acetic acid is hydrogenated at 3 atmospheres pressure and room temperature to yield 3-phosphonopiperidine-2-carboxylic acid, mp 150° dec.

The starting material is prepared as follows:

A solution of 1.5g of 3-diethylphosphonopyridine, Bull. Chem. Soc. Jap. 55, 909 (1982), in 20 ml of methylene chloride is treated with 2.33g m-chloroperbenzoic acid at room temperature. The reaction mixture is allowed to stir at room temperature overnight, then concentrated under vacuum. The residue is partitioned between ether and water, the aqueous layer is concentrated under vacuum to afford 3-(diethylphosphono)-pyridine-N-oxide as a yellow oil.

A solution of 1.2 g of the above intermediate in 5 ml $CHCl_3$ is treated with 3.0 ml triethylamine and 3.0 ml trimethylsilyl cyanide and heated under reflux under $N_2$ atmosphere for 15 hours. The reaction mixture is then cooled to room temperature, concentrated under vacuum, and the residue is partitioned between ethyl acetate and 0.1N NaOH. The organic layer is washed with saturated sodium chloride solution and dried over anhydrous magnesium sulfate. The crude product mixture is separated by flash column chromatography on silica gel, eluting with ethyl acetate: hexane (1:1) containing 1% methanol, to yield 2-cyano-3-diethylphosphonopyridine and 2-cyano-2-diethylphosphonopyridine.

A solution of 690 mg of 2-cyano-3-diethylphosphonopyridine in 8N hydrochloric acid is heated under reflux for 4 hours. The solvent is removed under vacuum and residue triturated with ethanol, filtered, and dried under vacuum to afford 3-phosphonopyridine-2-carboxylic acid hydrochloride, m.p. 251°-255°.

b) Similarly prepared is 5-phosphonopiperidine-2-carboxylic acid starting with 2-cyano-5-diethylphosphonopyridine which is prepared as described under a).

EXAMPLE 28

At $-78°$, 20.3 ml of butyllithium (1.64M) is added to 8.5 ml of tetraethylmethylenediphosphonate [bis(diethylphos phono)-methane]in 100 ml anhydrous tetrahydrofuran. After 5 minutes, 9.26 g of 1-tert-butoxycarbonyl-2-ethoxycarbonyl piperidine-4-acetaldehyde in 125 ml anhydrous tetrahydrofuran is added. Mixture is refluxed 18 hours, cooled, concentrated and purified by flash chromatography using ethyl acetate/hexane (75:25 to 9:1) to yield ethyl 4-[1-(3-diethylphosphonoprop-2-enyl)]-1-(tert-butoxycarbonyl)-piperidine-2-carboxylate.

The starting material is prepared as follows:

A solution of 4-pyridylacetic acid in 500 ml of anhydrous ethanol containing 75 ml of concentrated sulfuric acid is refluxed 18 hours. The solution is cooled to 0° an neutralized by addition of sodium hydroxide solution and saturated aqueous sodium carbonate. Extraction with ethyl acetate yields on concentration in vacuo ethyl 4-pyridylacetate.

A solution of 23.8 g of ethyl 4-pyridylacetate in 100 ml of anhydrous tetrahydrofuran is added dropwise to 5.5 g of lithium aluminum hydride in 150 ml of anhydrous tetrahydrofuran under nitrogen. The mixture is heated at 50° (bath) for 40 minutes, then cooled in an ice bath, and the excess lithium aluminum hydride is decomposed by addition of 6.6 ml of water followed by 6.6 ml of 15% aqueous sodium hydroxide and 20 ml of water. The solid is filtered off and the filtrate concentrated in vacuo to yield 4-pyridylethanol.

A solution of 16.3 g of 4-pyridylethanol, 21.8 g of chloro-tert-butyl-dimethylsilane and 10.9 g of imidazole in 150 ml of dimethylformamide is stirred 1 hour at room temperature. The product is isolated by extraction into ethyl acetate/hexane (1:1) and washed 4 times with 400 ml of water; the extract is filtered through silica gel and concentrated in vacuo to yield 4-(tert-butyl-dimethylsilyloxyethyl)-pyridine.

To a stirred solution of 28.8 g of 4-(tert-butyl-dimethylsilyloxyethyl)-pyridine in 300 ml of methylene chloride is added 24 g of m-chloroperbenzoic acid. After 4 hours the solution is washed with aqueous sodium carbonate solution and water. The solution is dried over sodium sulfate, filtered and concentrated in vacuo to yield 4-(tert-butyl-dimethylsilyloxyethyl)-pyridine-N-oxide.

A solution of 28.6 g of 4-(tert-butyl-dimethylsilyloxyethyl)-pyridine-N-oxide, 60.3 ml of trimethylsilyl cyanide and 31.5 ml triethylamine is stirred under nitrogen at reflux for 3 hours. The dark solution is cooled in an ice bath, 30 ml of ethanol added, followed by 400 ml ethyl acetate and 200 ml hexane. The solution is washed twice with 150 ml of water, dried over sodium sulfate, filtered, concentrated in vacuo and purified by flash chromatography using ethyl acetate/hexane (1:10) to yield 4-(tert-butyl-di-methylsilyloxyethyl)-2-cyanopyridine.

A solution of 22.2 g of 4-(tert-butyl-dimethylsilyloxyethyl)-2-cyanopyridine in 220 ml anhydrous ethanol containing 0.19 g of sodium is stirred at room temperature for 24 hours. The solution is then cooled to 0° and 22 ml of 6N hydrochloric acid added. The solution is stirred at room temperature for 16 hours, cooled to 0° and 7.5 ml 6N sodium hydroxide added followed by 75 ml saturated aqueous sodium bicarbonate. Extraction with methylene chloride and flash chromatography using ethyl acetate yields ethyl 4-(2-hydroxyethyl)-pyridine-2-carboxylate.

A mixture of 8.37 g of ethyl 4-(2-hydroxyethyl)-pyridine-2-carboxylate in 130 ml acetic acid and 4 g platinum oxide is hydrogenated at 50 lbs/in2. Filtration, concentration in vacuo, neutralization with potassium carbonate and extraction with methylene chloride yields an oil that is purified by flash chromatography using methylene chloride/methanol saturated with ammonia (20:1) to yield ethyl 4-(2-hydroxyethyl)-piperidine-2-carboxylate.

A solution of 7.9 g of ethyl-4-(2-hydroxyethyl)-piperidine-2-carboxylate, 9.0 g di-tert-butyl dicarbonate in 80 ml of methylene chloride is stirred for 2 hours at room temperature and then concentrated in vacuo to yield ethyl 1-(tert-butoxycarbonyl)-4-(2-hydroxyethyl)-piperidine-2-carboxylate.

A solution of 11.8 g of ethyl 1-tert-butoxycarbonyl-4-(2-hydroxyethyl)-piperidine-2-carboxylate and 12.6 g of pyridinium chlorochromate in 175 ml methylene chloride is stirred under nitrogen at room temperature for 80 minutes. Mixture is filtered and purified by flash chromatography using ethyl acetate/hexane (25:75) to yield 1-(tert-butoxycarbonyl)-2-ethoxycarbonyl-piperidine-4-acetaldehyde.

EXAMPLE 29

A mixture of 4.67 g of ethyl 4-[1-(3-diethylphosphonoprop-2-enyl]-1-tert-butoxycarbonyl-piperidine-2-carboxylate and 75 ml 6N hydrochloric acid is refluxed 12 hours. The solution is concentrated in vacuo to dryness. The residue is dissolved in 50 ml ethanol and 3.8 ml of propylene oxide added. The solid that separates is filtered off and dried in vacuo to yield cis-4-[1-(3-phosphonoprop-2-enyl]-piperidine-2-carboxylic acid, m.p. 163°-165°.

EXAMPLE 30

At −78°, 6.9 ml of butyllithium (1.6M) is added to 2.9 ml of tetraethylmethylene diphosphonate in 30 ml anhydrous tetrahydrofuran. After 5 minutes, 2.47 g of trans ethyl 1-acetyl-piperidine-2-carboxylate-4-acetaldehyde in 55 ml tetrahydrofuran (anhydrous) is added. The mixture is refluxed 18 hours, cooled, concentrated and purified by flash chromatography using methylene chloride/ethanol (100:3) to yield trans ethyl 4-[1-(3-diethylphosphonoprop-2-enyl)]-1-acetyl-piperidine-2-carboxylate.

The starting material is prepared as follows:

At 0°, 9.4 ml acetic anhydride is added to a stirred solution of 13.5 g of ethyl 4-(2-hydroxyethyl)-piperidine-2-carboxylate in 75 ml pyridine. After stirring at room temperature for 30 minutes the solution is concentrated in vacuo and ethyl acetate (300 ml) is added; the solution is washed twice with 2N hydrochloric acid, once with water and once with saturated sodium bicarbonate, dried over sodium sulfate, filtered and concentrated in vacuo. The residue is dissolved in 100 ml ethanol, 5 g of powdered potassium carbonate is added and the mixture stirred 1 hour at room temperature. The solution is filtered, concentrated in vacuo and purified by flash chromatography using methylene chloride/methanol (95:5) to yield trans ethyl 1-acetyl-4-(2-hydroxyethyl)-piperidine-2-carboxylate.

A mixture of 3.7 g of trans ethyl 1-acetyl-4-(2-hydroxy-ethyl)-piperidine-2-carboxylate and 5.4 g of pyridinium chlorochromate in 75 ml methylene chloride is stirred under nitrogen for 2 hours. The mixture is filtered and purified by flash chromatography using ethyl acetate/hexane (7:3 to 8:2) to yield trans ethyl 1-acetylpiperidine-2-carboxylate-4-acetaldehyde.

EXAMPLE 31

A mixture of 2.5 g of trans ethyl 4-[1-(3-diethylphosphono-prop-2-enyl)]-1-acetylpiperidine-2-carboxylate and 40 ml 6N hydrochloric acid is refluxed for 12 hours. The solution is concentrated in vacuo to dryness. The residue is dissolved in 20 ml of ethanol and 2.3 ml of propylene oxide added. The solid that separates is filtered off and dried in vacuo to yield trans 4-[1-(3-phosphonoprop-2enyl)]-piperidine-2-carboxylic acid, m.p. 132°-140°.

EXAMPLE 32

A solution of 0.334 g of trans ethyl 4-[1-(3-bromoprop-1-enyl)]-1-(tert-butoxycarbonyl)-piperidine-2-carboxylate and 3.5 ml of triethylphosphite is refluxed under nitrogen for 70 minutes. The cooled solution is concentrated in vacuo and purified by flash chromatography using methylene chloride/methanol (100:3) to yield trans ethyl 4-[1-(3-diethylphosphonoprop-1-enyl)]-1-(tert-butoxycarbonyl)-piperidine-2-carboxylate.

The starting material is prepared as follows:

A solution of 20 g 4-pyridylcarbinol, 28.9 g of chloro-tert-butyl-dimethylsilane and 14.4 g imidazole in 200 ml dimethylformamide is stirred 3 hours at room temperature. Product is isolated by extraction into ethyl acetate/hexane (1:1) and washing extract 4 times with 400 ml of water. The solution is filtered through silica gel and concentrated in vacuo to yield 4-(tert-butyl-dimethylsilyloxymethyl)pyridine.

A solution of 40.6 g of 4-(tert-butyl-dimethylsilyloxymethyl)-pyridine and 40 g of m-chloroperbenzoic acid in 500 ml methylene chloride is stirred 16 hours at room temperature. Solution is washed with 2N sodium hydroxide and water, dried over sodium sulfate, filtered and concentrated in vacuo to yield 4-(tert-butyldimethylsilyloxymethyl)-pyridine-N-oxide.

A solution of 37.9 g of 4-(tert-butyl-dimethylsilyloxymethyl)-pyridine-N-oxide, 84 ml of trimethylsilyl cyanide and 44 ml triethylamine is stirred under nitrogen at reflux for 2½ hours Dark solution is cooled in an ice bath, then 40 ml of ethanol added followed by 500 ml of ethyl acetate. The solution is washed twice with water, dried over sodium sulfate, filtered, concentrated in vacuo and purified by flash chromatography using ethyl acetate/hexane (1:10) to yield 4-(tert-butyl-dimethylsilyloxymethyl)-2-cyanopyridine.

A solution of 21.7 g of 4-(tert-butyl-dimethylsilyloxymethyl)-2-cyanopyridine in 220 ml anhydrous ethanol containing 0.2 g of sodium is stirred at room temperature for 18 hours, cooled to 0° and 22 ml 6N hydrochloric acid is then added. The solution is stirred at room temperature for 18 hours cooled to 0°, 7.5 ml 6N sodium hydroxide added followed by 20 ml saturated aqueous sodium carbonate. Extraction with methylene chloride, then drying, filtering and concentrating the extract yields an oil which crystallizes from ether to yield ethyl 4-(hydroxymethyl)-pyridine-2-carboxylate.

A mixture of 13.9 g of ethyl 4-(hydroxymethyl)-pyridine-2-carboxylate, 5 g platinum oxide in 250 ml acetic acid is hydrogenated at 50 lbs/in$^2$ Filtration, concentration in vacuo, and neutralization with potassium carbonate in methylene chloride yields an oil that is purified by flash chromatography using methylene chloride/methanol saturated with ammonia (20:1) to yield ethyl 4-(hydroxymethyl)-piperidine-2-carboxylate.

A solution of 5.16 g of ethyl 4-(hydroxymethyl)-piperidine-2-carboxylate and 6.33 g di-tert-butyl dicarbonate in 100 ml of methylene chloride is stirred at room temperature for 18 hours. The solution is concentrated in vacuo to yield ethyl 1-(tert-butoxycarbonyl)-4-(hydroxymethyl)-piperidine-2-carboxylate.

A solution of 7.9 g of ethyl 1-(tert-butoxycarbonyl)-4-(hydroxymethyl)-piperidine-2-carboxylate and 9.9 g of pyridinium chlorochromate in 175 ml of methylene chloride is stirred at room temperature for 3 hours. The mixture is filtered and purified by flash chromatography using ethyl acetate/hexane (25:75) to yield 1-(tert-butoxycarbonyl)-2-ethoxycarbonylpiperidine-4-carboxaldehyde.

A solution of 1 g of 1-(tert-butoxycarbonyl)-2-ethoxycarbonylpiperidine-4-carboxaldehyde and 2 g of formylmethylene-triphenylphosphoran in 16 ml of toluene is heated to 100° (bath) for 2 hours. The solution is cooled and purified by flash chromatography using ethyl acetate/hexane (25:75) to yield 1-(tert-butoxycarbonyl)-2-ethoxycarbonylpiperidine-4-acrylaldehyde.

A solution of 0.83 g of 1-tert-butoxycarbonyl-2-ethoxycarbonyl-piperidine-4-acrylaldehyde and 0.11 g of sodium borohydride in 8 ml of ethanol is stirred at 0° for 30 minutes; 0.2 ml of acetic acid is added followed by ice cold water and the mixture is extracted with methylene chloride. The extract is dried over sodium sulfate, filtered and concentrated in vacuo. Purification by flash chromatography using ethylacetate/hexane (25:75) yields trans ethyl 1-(tert-butoxycarbonyl)-4-[1-(3-hydroxyprop-1-enyl)]-piperidine-2-carboxylate.

A solution of 0.367 g of ethyl 1-tert-butoxycarbonyl-4-[1-(3-hydroxyprop-1-enyl)]-piperidine-2-carboxylate, 0.35 g triphenylphosphine and 0.23 of bromosuccinimide in 8 ml of methylene chloride is stirred initially at 0° and then at room temperature for 40 minutes. Purification by flash chromatography using ethyl acetate/hexane (1:9) yields trans ethyl 4-[1-(3-bromoprop-1-enyl)]-1-(tert-butoxycarbonyl)-piperidine-2-carboxylate.

EXAMPLE 33

A solution of 0.39 g of trans ethyl 4-1-(3-diethylphosphono-prop-1-enyl)]-1-(tert-butoxycarbonyl)-piperidine-2-carboxylate and 2.3 ml of trifluoroacetic acid in 8 ml of methylene chloride is stirred at room temperature for 30 minutes. Saturated aqueous sodium bicarbonate is added and the mixture extracted with methylene chloride. Purification by flash chromatography using methylene chloride/methanol saturated with ammonia (20:1) yields trans ethyl 4-[1-(3-diethylphosphonoprop-1-enyl)]-piperidine-2-carboxylate.

EXAMPLE 34

A solution of 0.265 g of trans ethyl 4-[1-(3-diethylphosphonoprop-1-enyl)]-piperidine-2-carboxylate in 5 ml of anhydrous ethanol containing 0.074 ml of butyl lithium (1.6M) is heated at 80° (bath) for 72 hours. After cooling, 0.025 ml acetic acid is added, followed by excess saturated sodium bicarbonate, and the mixture is extracted with methylene chloride. The methylene chloride extract on concentration is vacuo yields an oil; purification by flash chromatography using methylene chloride/isopropanol saturated with ammonia (20:1) yields cis ethyl 4-[1-(3-diethylphosphonoprop-1-enyl)]-piperidine-2-carboxylate.

EXAMPLE 35 a) A mixture of 0.142 g of cis ethyl 4-[1-(3-diethylphosphonoprop-1-enyl]-piperidine-2-carboxylate and 2.5 ml of 6N hydrochloric acid is refluxed for 12 hours. The solution is concentrated in vacuo to dryness. The residue is dissolved in 2 ml of ethanol and 0.15 ml of propylene oxide is added. The solid that separates is filtered off and dried in vacuo to yield cis 4-[1-(3-phosphonoprop-1-enyl)]-piperidine-2-carboxylic acid, m.p. 175° dec.; hydrochloride salt, m.p. 130° dec.

b) Similarly, hydrolysis of the trans ester of example 33 yields the corresponding trans acid, m.p. 130°-135°.

c) A solution of cis 4-[1-(3-phosphonoprop-1-enyl)]-piperidine-2-carboxylic acid in saturated ethanolic hydrochloric acid is heated under reflux overnight. The solvent is removed in vacuo. A solution of the residue in ethanol is treated with propylene oxide and evaporated to dryness to yield cis ethyl 4-[1-(3-phosphonoprop-1-enyl)]-piperidine-2-carboxylate.

EXAMPLE 36

To a solution of 0.234 g of trans 1-ethoxycarbonyl-2-ethoxycarbonyl-pyrrolidine-3-propionaldehyde in 5 ml of anhydrous tetrahydrofuran under nitrogen, cooled to −78°, is added slowly a solution of 0.23 ml of tetraethylmethylenediphosphonate and 0.57 ml of butyllithium (1.6M) in 5 ml of anhydrous tetrahydrofuran also at −78°. Solution is refluxed for 14 hours, cooled and treated with 0.15 ml of acetic acid; the reaction mixture is concentrated, diluted with water and extracted with methylene chloride. The extract is dried over sodium sulfate, filtered and concentrated; purification by flash chromatography using ethyl acetate yields trans ethyl 1-ethoxycarbonyl-3-[1-(4-diethylphosphonobut-3-enyl)]-pyrrolidine-2-carboxylate.

The starting material is prepared as follows:

A mixture of 50 g of N-(2-cyanoethyl)glycine in 300 ml of ethanol saturated with hydrogen chloride gas is stirred 1 hour at room temperature then refluxed for 1 hour. After cooling the solid is filtered off and the filtrate neutralized with sodium bicarbonate, filtered again and concentrated to yield ethyl N-(ethoxycarbonylmethyl)-β-alaninate.

To a mixture of 49 g of ethyl N-(ethoxycarbonylmethyl)-β-alaninate and 30 ml of water cooled to −10° is added dropwise 27.6 ml of ethyl chloroformate followed by a solution of 12.7 g of sodium carbonate in 50 ml of water. The mixture is warmed to room temperature then heated at 55° for 50 minutes. The mixture is cooled, extracted with toluene, the extract is washed with 2N hydrochloric acid and water. The extract is dried over sodium sulfate, filtered, concentrated and distilled in vacuo to yield ethyl N-(ethoxycarbonylmethyl)-N-(ethoxycarbonyl)-β-alaninate.

A solution of 53.9 g of ethyl N-(ethoxycarbonylmethyl)-N-(ethoxycarbonyl)-β-alaninate in 200 ml of toluene is added dropwise to a stirred solution of potassium hexamethyldisilazide (429 ml, 0,653 M) in 125 ml of toluene under nitrogen and cooled to 0°. After 45 minutes at 0°, 21.6 ml of acetic acid is added followed by a solution of 100 g of sodium phosphate (monobasic) in 1 liter of water. The layers are separated, the organic layer is washed with pH 7 buffer, dried over sodium sulfate, filtered, concentrated and purified by flash chromatography using ethyl acetate/hexane (3:7) to yield ethyl 1-ethoxycarbonyl-3-oxo-pyrrolidine-2-carboxylate.

To a stirred suspension of 24 g of benzyloxycarbonylmethyl-triphenylphosphonium bromide in 225 ml of anhydrous tetrahydrofuran under nitrogen and cooled to 0° is added 73 ml of potassium hexamethyldisilazide (0.652 M). After 10 minutes a solution of 11 g of ethyl 1-ethoxycarbonyl-3-oxopyrrolidine-2-carboxylate in 50 ml of tetrahydrofuran is added and the mixture refluxed 2½ hours. After cooling the mixture is filtered and concentrated in vacuo. The residue is dissolved in ethyl acetate, washed with water, dried over sodium sulfate, filtered, concentrated and purified by flash chromatography using ethyl acetate/hexane (1:4) to yield an oil; this is hydrogenated in 200 ml of ethanol and 5 g of 10% palladium on carbon to yield, after filtering and concentrating the filtrate, 1-ethoxycarbonyl-2-ethoxycarbonyl-pyrrolidine-3-acetic acid.

A solution of 10 g of 1-ethoxycarbonyl-2-ethoxycarbonyl-pyrrolidine-3-acetic acid in 50 ml tetrahydrofuran is cooled to 0° and 55 ml of borane/tetrahydrofuran (1 M) is added dropwise. After stirring 2 hours at 0°, 20 ml of water is added, the mixture is extracted with ethyl acetate, washed twice with water and dried over sodium sulfate. The solution is filtered, concentrated and purified by flash chromatography using ethyl acetate/hexane (1:1 to 7:3) to yield cis 1-ethoxycarbonyl-2-ethoxycarbonylpyrrolidine-3-ethanol.

A solution of 6 g of cis 1-ethoxycarbonyl-2-ethoxycarbonylpyrrolidine-3-ethanol in 75 ml of methylene chloride containing 7.3 ml of diisopropylethylamine, to which is added 5.1 ml of 85% benzyloxymethyl chloride, is stirred 3½ hours at room temperature. The solution is washed with water and saturated aqueous sodium bicarbonate. The solution is then dried over sodium sulfate, filtered, concentrated and purified by flash chromatography using ethyl acetate/hexane (1:4) to yield cis ethyl 1-ethoxycarbonyl-3-[2-(benzyloxymethoxy)-ethyl]-pyrrolidine-2-carboxylate.

A solution of 6.2 g of cis ethyl 1-ethoxycarbonyl-3-[2-(benzyloxymethoxy)-ethyl]-pyrrolidine-2-carboxylate in 75 ml of anhydrous ethanol containing 1 ml of butyllithium (1.6 M) is refluxed under nitrogen for 6 days. After cooling, 1.7 ml of 1N hydrochloric acid is added, the solution is concentrated in vacuo, cold water added and mixture extracted with methylene chloride. The extract is dried over sodium sulfate, filtered, concentrated and purified by high pressure liquid chromatography using ethyl acetate/hexane (15:85) to yield trans ethyl 1-ethoxycarbonyl-3-[2-(benzyloxymethoxy)-ethyl]-pyrrolidine-2-carboxylate.

A mixture of 1.64 g of trans ethyl 1-ethoxycarbonyl-3-[(2-benzyloxymethoxy)-ethyl]-pyrrolidine-2-carboxylate and 2 g of 10% palladium on carbon in 35 ml of acetic acid is hydrogenated at 45 lbs/in2 The mixture is filtered, concentrated in vacuo and purified by flash chromatography using ethyl acetate/hexane (6:4 to 7:3) to yield trans 1-ethoxycarbonyl-2-ethoxycarbonylpyrrolidine-3-ethanol.

A solution of 0.991 g of trans 1-ethoxycarbonyl-2-ethoxycarbonylpyrrolidine-3-ethanol and 1.24 g pyridinium chlorochromate in 20 ml of methylene chloride is stirred under nitrogen for 4 hours. Mixture is filtered and purified by flash chromatography using ethyl acetate/hexane (1:1) to yield trans 1-ethoxycarbonyl-2-ethoxycarbonylpyrrolidine-3-acetaldehyde.

To 0.4 g of trans 1-ethoxycarbonyl-2-ethoxycarbonylpyrrolidine-3-acetaldehyde in 5 ml anhydrous tetrahydrofuran under nitrogen, cooled to −78°, is added dropwise a solution of 1.17 g of methoxymethyl-triphenylphosphonium chloride in 15 ml of anhydrous tetrahydrofuran to which is added 1.55 ml of potassium tert-butoxide/tetrahydrofuran (1.6M). Solution is stirred at room temperature for 4 hours. 2N Hydrochloric acid (11 ml) is added and the mixture is stirred for 45 minutes. The solution is concentrated and then extracted with methylene chloride. The extract is dried over sodium sulfate, filtered, concentrated, and the residue is purified by flash chromatography using ethyl acetate/hexane (1:5 to 3:7) to yield trans 1-ethoxycarbonyl-2-ethoxycarbonylpyrrolidine-3-propionaldehyde.

EXAMPLE 37

A mixture of 0.193 g of trans ethyl 1-ethoxycarbonyl-3-[1-(4-diethylphosphonobut-3-enyl)]-pyrrolidine-2-carboxylate and 4 ml of concentrated hydrochloric acid is refluxed for 16 hours. The solution is cooled and concentrated to dryness in vacuo. The solid that separates is filtered off and dried in vacuo to yield trans 3-[1-(4-phosphonobut-3enyl)]-pyrrolidine-2-carboxylic acid, m.p. 110°-115° dec.

EXAMPLE 38

To a solution of 0.426 g of cis 1-ethoxycarbonyl-2-ethoxycarbonylpyrrolidine-3-propionaldehyde in 10 ml of anhydrous tetrahydrofuran under nitrogen, cooled to −78°, is added slowly a solution of 0.45 ml of tetraethylmethylenediphosphonate and 1.06 ml of butyllithium (1.6 M) in 10 ml of anhydrous tetrahydrofuran also at −78°. Solution is refluxed 14 hours, cooled and 0.3 ml acetic acid is added; the reaction mixture is concentrated, water is added and the mixture is extracted with methylene chloride. The extract is dried over sodium sulfate, filtered, concentrated and purified by flash chromatography using ethyl acetate to yield cis ethyl 1-ethoxycarbonyl-3-[1-(4-diethylphosphono-but-3-enyl)]-pyrrolidine-2-carboxylate.

The starting material is prepared as follows:

A solution of 0.908 g of cis 1-ethoxycarbonyl-2-ethoxycarbonylpyrrolidine-3-ethanol and 1.14 g pyridinium chlorochromate in 20 ml of methylene chloride is stirred under nitrogen for 4 hours. Mixture is filtered and purified by flash chromatography using ethyl acetate/hexane (1:1) to yield cis 1-ethoxycarbonyl-2-ethoxycarbonylpyrrolidine-3-acetaldehyde.

To 0.663 g of cis 1-ethoxycarbonyl-2-ethoxycarbonyl-pyrrolidine-3-acetaldehyde in 10 ml anhydrous tetrahydrofuran under nitrogen, cooled to −78°, is added dropwise a solution of 2.21 g of methoxymethyl-triphenylphosphonium chloride in 20 ml of anhydrous tetrahydrofuran to which is added 2.6 ml of potassium tert-butoxide/tetrahydrofuran (1.6M). Solution is stirred at room temperature for 4 hours; 15 ml of 2N hydrochloric acid is added and the mixture stirred for 45 minutes. The solution is concentrated and then extracted with methylene chloride. The extract is dried over sodium sulfate, filtered and concentrated; purification by flash chromatography using ethyl acetate/hexane (1:5 to 3:7) yields cis 1-ethoxycarbonyl-2-ethoxycarbonylpyrrolidine-3-propionaldehyde.

EXAMPLE 39

A mixture of 0.176 g of cis ethyl 1-ethoxycarbonyl-3-[1-(4-diethylphosphonobut-3-enyl)]-pyrrolidine-2-carboxylate and 3.5 ml of concentrated hydrochloric acid is refluxed 18 hours. The solution is concentrated in vacuo to dryness, the residue dissolved in 1.5 ml of isopropanol/methanol (5:1) and 0.2 ml of propylene oxide is added. The solid that separates is filtered off and dried in vacuo to yield cis 3-[1-(4-phosphonobut-3-enyl)]-pyrrolidine-2-carboxylic is acid, m.p. 132°-140°.

EXAMPLE 40

A solution of 0.0655 g of trans ethyl 1-ethoxycarbonyl-3-[1-(4-bromobut-2-enyl)-pyrrolidine-2-carboxylate in 0.75 ml of triethylphosphite is refluxed 20 minutes. The solution is concentrated in vacuo and the residue purified by flash chromatography using methylene chloride/ethanol (30:1) to yield trans ethyl 1-ethoxycarbonyl-3-[1-(4-di-ethylphosphono-but-2-enyl)]-pyrrolidine-2-carboxylate.

The starting material is prepared as follows:

A solution of 0.225 g of trans 1-ethoxycarbonyl-2-ethoxycarbonylpyrrolidine-3-acetaldehyde and 0.4 g of (formylmethylene)-triphenylphosphoran in 2 ml of methylene chloride is refluxed 44 hours. The solution is concentrated and the residue is purified by flash chromatography using ethyl acetate/hexane (2:3) to yield trans ethyl 1-ethoxycarbonyl-3-[1-(4-oxobut-2-enyl)]-pyrrolidine-2-carboxylate.

To a stirred solution of 0.102 g of trans ethyl 1-ethoxycarbonyl-3-[1(4-oxobut-2-enyl)]-pyrrolidine-2-carboxylate in 2 ml of ethanol cooled to 0° is added 0.035 g of sodium borohydride. After 30 minutes at 0° and 30 minutes at room temperature 0.05 ml of acetic acid is added, the solution concentrated, water added and mixture extracted with methylene chloride. The solution is dried over sodium sulfate, filtered and concentrated in vacuo to yield trans ethyl 1-ethoxycarbonyl-3-[1-(4-hydroxybut-2-enyl)]-pyrrolidine-2-carboxylate.

To a stirred solution of .0937 g of trans ethyl-1-ethoxycarbonyl-3-[1-(4-hydroxybut-2-enyl)]-pyrrolidine-2-carboxylate and 0.1 g of triphenylphosphine in 2 ml of methylene chloride at 0° is added 0.067 g of N-bromosuccinimide. After 30 minutes at room temperature the mixture is purified by flash chromatography using ethyl acetate/hexane (1:3) to yield trans ethyl 1-ethoxycarbonyl-3-[1-(4-bromobut-2-enyl)]-pyrrolidine-2-carboxylate.

EXAMPLE 41

A mixture of 0.053 g of trans ethyl 1-ethoxycarbonyl-3-[1-(4-diethylphosphonobut-2-enyl)-pyrrolidine-2-carboxylate and 1.5 ml of concentrated hydrochloric acid is refluxed for 16 hours. The solution is concentrated to dryness in vacuo, the residue is dissolved in 1 ml of methanol, 0.2 ml of propylene oxide is added and the solution is concentrated. The residue is purified by ion exchange chromatography eluting with 0.1 N ammonium hydroxide to yield trans 3-[1-(4-phosphonobut-2-enyl)]-pyrrolidine-2-carboxylic acid, m.p. 138°-145°.

EXAMPLE 42

Preparation of an injectable formulation containing 10 mg of the active ingredient per 5 ml of solution having a formula as follows:

| | |
|---|---|
| cis 4-[1-(3-phosphonoprop-1-enyl)]-piperidine-2-carboxylic acid | 10.0 g |
| Propylparaben | 0.5 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 43 a) Preparation of 10,000 tablets each containing 10 mg of the active ingredient, having the formula as follows:

| | |
|---|---|
| cis 4-[1-(3-phosphonoprop-1-enyl)]-piperidine-2-carboxylic acid | 100.00 g |
| Lactose | 2,535.00 g |

-continued

| | |
|---|---|
| Corn starch | 125.00 g |
| Polyethylene glycol 6,000 | 150.00 g |
| Magnesium stearate | 40.00 g |
| Purified water | q.s. |

Procedure

All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35° C broken on a screen with 1.2 mm openings and compressed into tablets, using concave punches uppers bisected.

Analogously tablets are prepared, containing about 1-50 mg of one of the other compounds disclosed and exemplified herein.

b) Preparation of 1,000 capsules each containing 5 mg of the active ingredient, having the formula as follows:

| | |
|---|---|
| cis 4-[1-(3-phosphonoprop-1-enyl)]-piperidine-2-carboxylic acid | 5.0 g |
| Lactose | 212.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filing machine.

Analogously capsules are prepared, containing about 1-50 mg of the other compounds disclosed and exemplified herein.

What is claimed is:

1. A compound of the formula VI

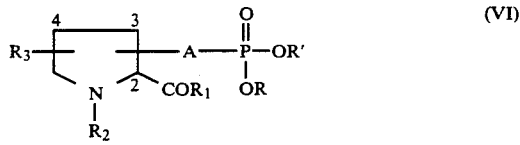

or with a double bond present between the 3 and 4 carbon atoms of the pyrrolidinyl ring, wherein R and R' represent hydrogen, lower alkyl, benzyl, benzyl substituted on phenyl by halogen, lower alkyl or lower alkoxy, or R and R' represent lower alkanoyloxymethyl, lower alkanoyloxymethyl substituted on oxymethyl by lower alkyl, cyclohexyl or cyclopentyl; $R_2$ represents hydrogen, lower alkyl or acyl; $R_3$ represents hydrogen, lower alkyl or aryl-lower alkyl; $COR_1$ represents carboxy, carbamoyl or carboxy esterified in form of a pharmaceutically acceptable prodrug ester; A represents lower alkylene or lower alkenylene; and in the above definitions acyl represents lower alkanoyl, aryl-lower alkanoyl, aroyl, lower alkoxycarbonyl, aryl-lower alkoxycarbonyl or alpha-amino-lower alkanoyl; aryl represents phenyl or phenyl substituted by one to three substituents selected from lower alkyl, lower alkoxy, trifluoromethyl and halogen; aroyl represents benzoyl or benzoyl substituted by one to three substituents selected from lower alkyl, lower alkoxy, trifluoromethyl and halogen; or a pharmaceutically acceptable salt thereof.

2. A compound according to claim 1 of formula VI wherein the phosphono bearing group is attached at the 3-position; $R_2$ and $R_3$ represent hydrogen; R and R' represent hydrogen; $COR_1$ represents carboxy or carboxy esterified in the form of a pharmaceutically acceptable prodrug ester; A represents methylene, ethylene or propylene; or a pharmaceutically acceptable salt thereof.

3. A compound according to claim 1 of formula VI wherein the phosphono bearing group A is attached at the 3-position; $R,R',R_2,R_3$ and $COR_1$ have meaning as defined above; and A represents 1,3-propenylene with double bond adjacent to the phosphono grouping, or a pharmaceutically acceptable salt thereof.

4. A compound according to claim 1 being trans 3-[1-(4-phosphonobut-3-enyl)]-pyrrolidine-2-carboxylic acid or a pharmaceutically acceptable salt thereof.

5. A compound according to claim 1 being trans 3-[1-(4-phosphonobut-2-enyl)]-pyrrolidine-2-carboxylic acid or a pharmaceutically acceptable salt thereof.

6. A compound according to claim 1 being cis 4-(2-phosphonoethyl)-pyrrolidine-2-carboxylic acid or a pharmaceutically acceptable salt thereof.

7. A compound according to claim 1 of formula VI wherein the phosphono bearing group is attached at the 3 or 4-position; $R_2$ and $R_3$ represent hydrogen; R and R' represent hydrogen or lower alkanoyloxymethyl; $COR_1$ represents carboxy, carbamoyl or carboxy esterified in form of a pharmaceutically acceptable prodrug ester; A represents methylene, ethylene, or propylene; $R_2$ represents hydrogen; or a pharmaceutically acceptable salt thereof.

8. A compound according to claim 7 being trans 3-phosphonoethylpyrrolidine-2-carboxylic acid or a pharmaceutically acceptable salt thereof.

9. A pharmaceutical composition suitable for the blockade of the N-methyl-D-aspartate excitatory amino acid receptor in a mammal comprising a correspondingly effective amount of a compound of claim 1 in combination with one or more pharmaceutically acceptable carriers.

10. A method of blocking the N-methyl-D-aspartate excitatory amino acid receptor in a mammal comprising the administration to a mammal in need thereof of a correspondingly effective amount of a compound of claim 1 or of a pharmaceutical composition comprising said compound.

11. A method of treating diseases responsive to N-methyl-D-aspartate excitatory amino acid receptor blockade in mammals comprising the administration to a mammal in need thereof of an effective N-methyl-D-aspartate excitatory amino acid receptor blocking amount of a compound of claim 1 or of a pharmaceutical composition comprising said compound.

* * * * *